(12) United States Patent
Suzuki et al.

(10) Patent No.: US 8,278,030 B2
(45) Date of Patent: Oct. 2, 2012

(54) SULFONIUM SALT, PHOTOACID GENERATOR, AND PHOTOCURABLE COMPOSITION AND CURED BODY THEREOF

(75) Inventors: Issei Suzuki, Kyoto (JP); Hideki Kimura, Kyoto (JP)

(73) Assignee: San-Apro Limited, Kyoto-shi (JP)

( * ) Notice: Subject to any disclaimer, the term of this patent is extended or adjusted under 35 U.S.C. 154(b) by 198 days.

(21) Appl. No.: 12/989,549

(22) PCT Filed: Apr. 27, 2009

(86) PCT No.: PCT/JP2009/001925
§ 371 (c)(1),
(2), (4) Date: Oct. 25, 2010

(87) PCT Pub. No.: WO2009/136482
PCT Pub. Date: Nov. 12, 2009

(65) Prior Publication Data
US 2011/0039205 A1    Feb. 17, 2011

(30) Foreign Application Priority Data
May 6, 2008    (JP) .................... 2008-120828

(51) Int. Cl.
G03F 7/029      (2006.01)
C07D 495/00     (2006.01)
C07D 335/04     (2006.01)
C08G 59/68      (2006.01)
C08F 2/50       (2006.01)

(52) U.S. Cl. ..... 430/922; 430/924; 430/914; 430/270.1; 430/280.1; 430/281.1; 430/9; 430/18; 549/27; 522/31; 522/53

(58) Field of Classification Search .................... None
See application file for complete search history.

(56) References Cited

U.S. PATENT DOCUMENTS

| | | | |
|---|---|---|---|
| 4,136,102 A | 1/1979 | Crivello |
| 4,161,478 A | 7/1979 | Crivello |
| 4,173,551 A | 11/1979 | Crivello |
| 4,175,972 A | 11/1979 | Crivello |
| 4,219,654 A | 8/1980 | Crivello |
| 4,234,732 A | 11/1980 | Crivello |
| 4,250,311 A | 2/1981 | Crivello |
| 4,273,668 A | 6/1981 | Crivello |
| 4,283,312 A | 8/1981 | Crivello |
| 4,407,759 A | 10/1983 | Crivello |
| 4,417,061 A | 11/1983 | Crivello |
| 6,093,753 A | 7/2000 | Takahashi |

FOREIGN PATENT DOCUMENTS

| | | | |
|---|---|---|---|
| JP | 50-151997 A | 12/1975 |
| JP | 2-178303 A | 7/1990 |
| JP | 8-165290 A | 6/1996 |
| JP | 9-1188663 A | 5/1997 |
| JP | 10-182711 | * 7/1998 |
| JP | 11-269212 | * 10/1999 |

OTHER PUBLICATIONS

Notification of Transmittal of Translation of the International Preliminary Report on Patentability (Form PCT/IB/338) of International Application No. PCT/JP2009/001925 mailed Dec. 23, 2010 with Forms PCT/IB/373 and PCT/ISA/237, (2010).
Allen, S. et al.; "Photochemistry and Photoinitiator Properties of Novel 1-Chloro-Substituted Thioxanthones-II. Influence of 4-oxy and 1-Phenylthio Substition"; Eur. Polym. J.; vol. 33; No. 10-12; pp. 1639-1643; 1997.
Ruhlmann, D. et al; "Relations Structure-Properties Dans Les Photoamorceurs De Polymerization-6. Interactions Avec Des Photosensibilisateurs"; Eur. Polym. J.; vol. 29; No. 1; pp. 27-34; 1993.

* cited by examiner

*Primary Examiner* — Sin J. Lee
(74) *Attorney, Agent, or Firm* — Westerman, Hattori, Daniels & Adrian, LLP

(57) ABSTRACT

An object of the present invention is to provide a sulfonium salt that has sufficient photosensitivity by active energy rays, such as visible light, ultraviolet rays, electron beams, and X-rays. The present invention is a sulfonium salt represented by formula (1). It is noted that $R^1$ is a group represented by formula (2); $R^2$ and $R^3$ each represent an aryl group having 6 to 30 carbon atoms, a heterocyclic hydrocarbon group having 4 to 30 carbon atoms, an alkyl group having 1 to 30 carbon atoms, an alkenyl group having 2 to 30 carbon atoms, or an alkynyl group having 2 to 30 carbon atoms; $X^-$ represents a monovalent polyatomic anion; $R^4$ to $R^6$ each represent an alkyl group, or the like; k represents an integer of 0 to 4; m represents an integer of 0 to 3; n represents an integer of 0 to 4; and A represents a group represented by —S—, —O—, —SO—, —SO_2—, or —CO—.

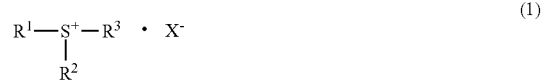

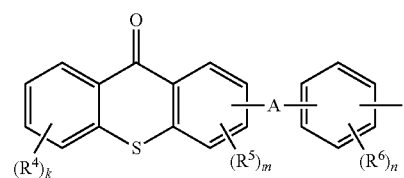

9 Claims, No Drawings

SULFONIUM SALT, PHOTOACID GENERATOR, AND PHOTOCURABLE COMPOSITION AND CURED BODY THEREOF

TECHNICAL FIELD

The present invention relates to a sulfonium salt, a photoacid generator, and a curable composition and a cured body thereof. More specifically, the present invention relates to a sulfonium salt that is suitable for curing a cationically polymerizable compound by applying active energy rays, such as light, electron beams, or X-rays, a photoacid generator containing this sulfonium salt, a curable composition containing this photoacid generator, and a cured body obtained by curing this curable composition.

BACKGROUND ART

As polymerization initiators to be used in curing a cationically polymerizable compound, such as an epoxy compound, by applying active energy rays, such as light, electron beams, or X-rays, there have been known triarylsulfonium salts (Patent Document 1), phenacylsulfonium salts having a naphthalene skeleton (Patent Document 2), dialkylbenzylsulfonium salts (Patent Document 3), and sulfonium salts resulting from the introduction of a thioxanthone skeleton into a sulfonium salt (Patent Document 4).

PRIOR ART DOCUMENTS

Patent Documents

Patent Document 1: JP 50-151997 A (corresponding U.S. Pat. Nos. 4,136,102, 4,161,478, 4,173,551, 4,175,972, 4,219,654, 4,234,732, 4,250,311, 4,273,668, 4,283,312, 4,407,759, and 4,417,061)
Patent Document 2: JP 9-118663 A (corresponding U.S. Pat. No. 6,093,753)
Patent Document 3: JP 2-178303 A
Patent Document 4: JP 8-165290 A

SUMMARY OF THE INVENTION

Problems to be Solved by the Invention

The triarylsulfonium salts (Patent Document 1), the phenacylsulfonium salts having a naphthalene skeleton (Patent Document 2), and the dialkylbenzylsulfonium salts (Patent Document 3) are so low in photosensitivity that cationically polymerizable compounds are not polymerized therewith at all by irradiation with visible light.

The sulfonium salts resulting from the introduction of a thioxanthone skeleton into a sulfonium salt (Patent Document 4) have a problem that they are insufficient in photosensitivity to irradiation with visible light {especially, the h-line (405 nm) and the g-line (436 nm) of a general purpose high pressure mercury lamp and long-wavelength laser beams}.

An object of the present invention is to provide a sulfonium salt that has sufficient photosensitivity by active energy rays, such as visible light, ultraviolet rays, electron beams, and X-rays.

Means for Solving the Problems

A gist of the feature of the sulfonium salt of the present invention is that it is represented by formula (1):

[Chem. 1]

$$R^1 - S^+ - R^3 \cdot X^- \atop | \atop R^2$$
(1)

wherein $R^1$ is a group represented by formula (2); $R^2$ and $R^3$ each represent an aryl group having 6 to 30 carbon atoms, a heterocyclic hydrocarbon group having 4 to 30 carbon atoms, an alkyl group having 1 to 30 carbon atoms, an alkenyl group having 2 to 30 carbon atoms, or an alkynyl group having 2 to 30 carbon atoms, wherein some hydrogen atoms of the aryl group, the heterocyclic hydrocarbon group, the alkyl group, the alkenyl group, or the alkynyl group may be substituted with a substituent (t); S represents a sulfur atom; and $X^-$ represents a monovalent polyatomic anion:

[Chem. 2]

(2)

wherein $R^4$ to $R^6$ each represent an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group, a cyano group, a nitro group, or a halogen atom; k, m, and n represent the number of $R^4$, the number of $R^5$, and the number of $R^6$, respectively; k is an integer of 0 to 4; m is an integer of 0 to 3; n is an integer of 0 to 4; A is a group represented by —S—, —O—, —SO—, —SO$_2$—, or —CO—; O represents an oxygen atom; and S represents a sulfur atom.

A gist of the feature of the photoacid generator of the present invention is that it contains the above-mentioned sulfonium salt.

A gist of the feature of the energy ray-curable composition of the present invention is that it contains the above-mentioned photoacid generator and a cationically polymerizable compound.

A gist of the feature of the cured body of the present invention is that it is obtained by curing the above-mentioned energy ray-curable composition.

Effect of the Invention

The sulfonium salt of the present invention is superior in photosensitivity by active energy rays, such as visible light, ultraviolet rays, electron beams, and X-rays.

The photoacid generator of the present invention is superior in ability to cure a cationically polymerizable compound by the action of active energy rays because it contains the above-mentioned sulfonium salt. The photoacid generator of the present invention can cure a cationically polymerizable compound by visible light even if no sensitizer is used because it contains the sulfonium salt superior in photosensitivity.

The energy ray-curable composition of the present invention can be cured by visible light because it contains the above-mentioned photoacid generator. The energy ray-curable composition of the present invention is superior in workability because it does not need the use of a sensitizer.

The cured body of the present invention does not exhibit coloring or degradation caused by the residual sensitizer because it contains no sensitizer.

Therefore, the sulfonium salt of the present invention is suitable as a photoacid generator to be used for paint, a coating agent, ink, resist (positive resist, chemically amplified resist, and negative resist), a resist film, a photosensitive material, an adhesive, a molding material, a casting material, putty, a glass fiber impregnant, a filler, a sealing material, a sealant, or a material of stereolithography. Moreover, the energy ray-curable composition and the cured body of the present invention are suitable for the above-mentioned applications.

MODE FOR CARRYING OUT THE INVENTION

In formula (1), $R^1$ is a group represented by formula (2), in which among $R^4$ to $R^6$, the alkyl group includes straight chain alkyl groups having 1 to 18 carbon atoms (methyl, ethyl, n-propyl, n-butyl, n-pentyl, n-octyl, n-decyl, n-dodecyl, n-tetradecyl, n-hexadecyl, n-octadecyl, and the like), branched alkyl groups having 1 to 18 carbon atoms (isopropyl, isobutyl, sec-butyl, tert-butyl, isopentyl, neopentyl, tert-pentyl, isohexyl, and isooctadecyl), and cycloalkyl groups having 3 to 18 carbon atoms (cyclopropyl, cyclobutyl, cyclopentyl, cyclohexyl, 4-decylcyclohexyl, and the like).

Among $R^4$ to $R^6$, the alkoxy group includes straight chain or branched alkoxy groups having 1 to 18 carbon atoms (methoxy, ethoxy, propoxy, isopropoxy, butoxy, isobutoxy, sec-butoxy, tert-butoxy, hexyloxy, decyloxy, dodecyloxy, octadecyloxy, and the like).

Among $R^4$ to $R^6$, the alkylcarbonyl group includes straight chain or branched alkylcarbonyl groups having 2 to 18 carbon atoms (acetyl, propionyl, butanoyl, 2-methylpropionyl, heptanoyl, 2-methylbutanoyl, 3-methylbutanoyl, octanoyl, decanoyl, dodecanoyl, octadecanoyl, and the like).

Among $R^4$ to $R^6$, the arylcarbonyl group includes arylcarbonyl groups having 7 to 11 carbon atoms (benzoyl, naphthoyl, and the like).

Among $R^4$ to $R^6$, the alkoxycarbonyl group includes straight chain or branched alkoxycarbonyl groups having 2 to 18 carbon atoms, 2 to 19 carbon atoms (methoxycarbonyl, ethoxycarbonyl, propoxycarbonyl, isopropoxycarbonyl, butoxycarbonyl, isobutoxycarbobutoxy, sec-butoxycarbonyl, tert-butoxycarbonyl, octyloxycarbonyl, tetradecyl oxycarbonyl, octadecyloxycarbonyl, and the like).

Among $R^4$ to $R^6$, the aryloxycarbonyl group includes aryloxycarbonyl groups having 7 to 11 carbon atoms (phenoxycarbonyl, naphthoxycarbonyl, and the like).

Among $R^4$ to $R^6$, the arylthiocarbonyl group includes arylthiocarbonyl groups having 7 to 11 carbon atoms (phenylthiocarbonyl, naphthoxythiocarbonyl, and the like).

Among $R^4$ to $R^6$, the acyloxy group includes straight chain or branched acyloxy groups having 2 to 19 carbon atoms (acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, octadecylcarbonyloxy, and the like).

Among $R^4$ to $R^6$, the arylthio group includes aryltio groups having 6 to 20 carbon atoms (phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthiophenylthio, 4-benzoyl-2-methylthiophenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl)phenylthio, 4-(p-tert-butylbenzoyl)phenylthio, and the like).

Among $R^4$ to $R^6$, the alkylthio group includes straight chain or branched alkylthio groups having 1 to 18 carbon atoms (methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, isooctadecylthio, and the like).

Among $R^4$ to $R^6$, the aryl group includes aryl groups having 6 to 10 carbon atoms (phenyl, tolyl, dimethylphenyl, naphthyl, and the like).

Among $R^4$ to $R^6$, the heterocyclic hydrocarbon group includes heterocyclic hydrocarbon groups having 4 to 20 carbon atoms (thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, and the like).

Among $R^4$ to $R^6$, the aryloxy group includes aryloxy groups having 6 to 10 carbon atoms (phenoxy, naphthyloxy, and the like).

Among $R^4$ to $R^6$, the alkylsulfinyl group includes straight chain or branched alkylsulfinyl groups having 1 to 18 carbon atoms (methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, tert-pentylsulfinyl, octylsulfinyl, isooctadecylsulfinyl, and the like).

Among $R^4$ to $R^6$, the arylsulfinyl group includes arylsulfinyl groups having 6 to 10 carbon atoms (phenylsulfinyl, tolylsulfinyl, naphthylsulfinyl, and the like).

Among $R^4$ to $R^6$, the alkylsulfonyl group includes straight chain or branched alkylsulfonyl groups having 1 to 18 carbon atoms (methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, octylsulfonyl, octadecylsulfonyl, and the like).

Among $R^4$ to $R^6$, the arylsulfonyl group includes arylsulfonyl groups having 6 to 10 carbon atoms (phenylsulfonyl, tolylsulfonyl (i.e., tosyl), naphthylsulfonyl, and the like).

Among $R^4$ to $R^6$, the hydroxy(poly)alkyleneoxy group includes hydroxyl(poly)alkyleneoxy groups represented by formula (3), and the like:

[Chem. 3]

HO(-AO)q- (3)

wherein AO represents an ethyleneoxy group and/or a propyleneoxy group, and q represents an integer of 1 to 5.

Among $R^4$ to $R^6$, the amino group includes an amino group ($-NH_2$) and substituted amino groups having 1 to 15 carbon atoms (methylamino, dimethylamino, ethylamino, methylethylamino, methylamino, n-propylamino, methyl-n-propylamino, ethyl-n-propylamino, di-n-propylamino, isopropylamino, isopropylmethylamino, isopropylethylamino, diisopropylamino, phenylamino, diphenylamino, methylphenylamino, ethylphenylamino, n-propylphenylamino, isopropylphenylamino, and the like).

Among $R^4$ to $R^6$, the halogen atom includes a fluorine atom, a chlorine atom, a bromine atom, and an iodine atom.

$R^4$ to $R^6$ may be all the same or different, or some of them may be different.

k, which represents the number of $R^4$, is an integer of 0 to 4, preferably 0 to 3, more preferably 0 to 2, particularly preferably 0 or 1. Moreover, m, which represents the number of $R^5$, is an integer of 0 to 3, preferably 0 to 2, more preferably 0 or 1. Furthermore, n, which represents the number of $R^6$, is an integer of 0 to 4, preferably 0 to 3, more preferably 0 to 2, particularly preferably 0 or 1. When being within such ranges, the photosensitivity of a sulfonium salt becomes better.

In formula (1), some hydrogen atoms of the aryl group, the heterocyclic hydrocarbon group, the alkyl group, the alkenyl group, or the alkynyl group ($R^2$, $R^3$) may be substituted with a substituent (t). The substituent (t) includes at least one member selected from the group consisting of an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy(poly)alkyleneoxy group, an amino group, a cyano group, a nitro group, and a halogen atom. The substituent (t) is the same as the substituents explained for $R^4$ to $R^6$.

Of $R^2$ and $R^3$, the aryl group having 6 to 30 carbon atoms includes monocyclic aryl groups and fused polycyclic aryl groups.

Examples of the monocyclic aryl groups include phenyl, hydroxyphenyl, toluoyl, dimethylphenyl, trimethylphenyl, ethylphenyl, diethylphenyl, triethylphenyl, n-propylphenyl, isopropylphenyl, n-butylphenyl, isobutylphenyl, sec-butylphenyl, tert-butylphenyl, methoxypheny, ethoxyphenyl, n-propoxyphenyl, isopropoxyphenyl, n-butoxyphenyl, isobutoxyphenyl, sec-butoxyphenyl, tert-butoxyphenyl, acetylphenyl, benzoylphenyl, naphthoylphenyl, phenylthiophenyl, naphthylthiophenyl, biphenylyl, phenoxyphenyl, naphthoxyphenyl, nitrophenyl, fluorophenyl, chlorophenyl, and bromophenyl.

Examples of the fused polycyclic aryl groups include naphthyl, anthracenyl, phenanthrenyl, pyrenyl, crycenyl, naphthacenyl, benzoanthracenyl, anthraquinolyl, fluorenyl, naphthoquinolyl, hydroxynaphthyl, methylnaphthyl, ethylnaphthyl, methoxynaphthyl, ethoxynaphthyl, acetylnaphthyl, benzoylnaphthyl, phenylthionaphthyl, phenylnaphthyl, phenoxynaphthyl, nitronaphthyl, fluoronaphthyl, chloronaphthyl, bromonaphthyl, hydroxyanthracenyl, methylanthracenyl, ethylanthracenyl, methoxyanthracenyl, ethoxyanthracenyl, acetylanthracenyl, benzoylanthracenyl, phenylthioanthracenyl, phenoxyanthracenyl, nitroanthracenyl, fluoroanthracenyl, chloroanthracenyl, and bromoanthracenyl.

Of $R^2$ and $R^3$, the heterocyclic hydrocarbon group having 4 to 30 carbon atoms includes cyclic hydrocarbon groups containing 1 to 3 hetero atoms (an oxygen atom, a nitrogen atom, a sulfur atom, and the like) in a ring, which include monocyclic heterocyclic hydrocarbon groups and fused polycyclic heterocyclic hydrocarbon groups.

Examples of the monocyclic heterocyclic hydrocarbon groups include thienyl, furanyl, pyranyl, pyrrolyl, oxazolyl, thiazolyl, pyridyl, pyrimidyl, pyrazinyl, hydroxythienyl, methylthienyl, ethylthienyl, methoxythienyl, acetylthienyl, benzoylthienyl, phenylthiothienyl, phenoxythienyl, nitrothienyl, fluorothienyl, chlorothienyl, bromothienyl, hydroxyfuranyl, methylfuranyl, ethylfuranyl, methoxyfuranyl, acetylfuranyl, benzoylfuranyl, phenylthiofuranyl, phenoxyfuranyl, nitrofuranyl, fluorofuranyl, chlorofuranyl, and bromofuranyl.

Examples of the fused polycyclic heterocyclic hydrocarbon groups include indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, hydroxyxanthenyl, methylxanthenyl, ethylxanthenyl, methoxyxanthenyl, acetylxanthenyl, benzoylxanthenyl, phenylthioxanthenyl, phenoxyxanthenyl, nitroxanthenyl, fluoroxanthenyl, chloroxanthenyl, bromoxanthenyl, hydroxythianthrenyl, methylthianthrenyl, ethylthianthrenyl, methoxythianthrenyl, benzoylthianthrenyl, phenylthiothianthrenyl, phenoxythianthrenyl, nitrothianthrenyl, fluorothianthrenyl, chlorothianthrenyl, bromothianthrenyl, hydroxyxanthonyl, methylxanthonyl, dimethylxanthonyl, ethylxanthonyl, diethylxanthonyl, n-propylxanthonyl, isopropylxanthonyl, methoxyxanthonyl, acetylxanthonyl, benzoylxanthonyl, phenylthioxanthonyl, phenoxyxanthonyl, acetoxyxanthonyl, nitroxanthonyl, fluoroxanthonyl, chloroxanthonyl, hydroxythioxanthonyl, methylthioxanthonyl, dimethylthioxanthonyl, ethylthioxanthonyl, diethylthioxanthonyl, n-propylthioxanthonyl, isopropylthioxanthonyl, methoxythioxanthonyl, acetylthioxanthonyl, benzoylthioxanthonyl, phenylthiothioxanthonyl, phenoxythioxanthonyl, acetoxythioxanthonyl, nitrothioxanthonyl, fluorothioxanthonyl, chlorothioxanthonyl, and bromothioxanthonyl.

Of $R^2$ and $R^3$, the alkyl group having 1 to 30 carbon atoms includes straight chain alkyl groups (methyl, ethyl, propyl, butyl, pentyl, octyl, decyl, dodecyl, tetradecyl, hexadecyl, octadecyl, benzyl, diphenylmethyl, naphthylmethyl, anthracenylmethyl, phenacyl ($-CH_2COC_6H_5$), naphthoylmethyl, anthoylmethyl, and the like), branched alkyl groups (isopropyl, isobutyl, sec-butyl, tert-butyl, isopentyl, neopentyl, tert-pentyl, isohexyl, and the like), and cycloalkyl groups (cyclopropyl, cyclobutyl, cyclopentyl, cyclohexyl, and the like).

Of $R^2$ and $R^3$, the alkenyl group having 2 to 30 carbon atoms includes straight chain alkenyl groups (vinyl, allyl, 1-propenyl, 1-butenyl, 1-pentenyl, 1-decenyl, 1-dodecenyl, and the like), and branched alkenyl groups (isopropenyl, 2-butenyl, 3-butenyl, 1-methyl-1-propenyl, 1-methyl-2-propenyl, 2-methyl-1-propenyl, 2-methyl-2-propenyl, 2-pentenyl, 3-pentenyl, 4-pentenyl, 1-methyl-1-butenyl, 2-methyl-2-butenyl, 3-methyl-2-butenyl, 1,2-dimethyl-1-propenyl, 2-decenyl, 8-decenyl, 2-dodecenyl, and 10-dodecenyl.

Of $R^2$ and $R^3$, the alkynyl group having 2 to 30 carbon atoms include straight chain alkynyl groups (ethynyl, 1-propynyl, 1-butynyl, 1-pentynyl, 1-decinyl, 1-dodecynyl, and the like) and branched alkynyl groups (2-propynyl, 2-butynyl, 3-butynyl, 1-methyl-1-propynyl, 1-methyl-2-propynyl, 2-methyl-1-propynyl, 2-methyl-2-propynyl, 2-pentynyl, 3-pentynyl, 4-pentynyl, 1-methyl-1-butynyl, 2-methyl-2-butynyl, 3-methyl-2-butynyl, 1,2-dimethyl-1-propynyl, 2-decynyl, 8-decynyl, 2-dodecynyl, 10-dodecynyl, 2-dodecynyl, 10-dodecynyl, and the like).

Of $R^2$ and $R^3$, the aryl groups having 6 to 30 carbon atoms of which some hydrogen atoms may be substituted with a substituent (t) and the heterocyclic hydrocarbon groups having 4 to 30 carbon atoms of which some hydrogen atoms may be substituted with a substituent (t) are preferred, the heterocyclic hydrocarbon groups having 4 to 30 carbon atoms are more preferred, the fused polycyclic heterocyclic hydrocarbon groups are particularly preferred, and thioxanthonyl is most preferred.

Among the sulfonium salts represented by formula (1), is preferred one in which $R^2$ or $R^3$ is an aryl group having 6 to 30 carbon atoms or a heterocyclic hydrocarbon group having 4 to 30 carbon atoms. Preferably, $R^2$ or $R^3$ is a phenyl group, A is a group represented by —S—, and k, m, and n are each 0. Preferably, $R^2$ or $R^3$ is a thioxanthonyl group, A is a group represented by —S—, and k, m, and n are each 0.

In formula (1), $X^-$, which has no restriction as far as being a monovalent polyatomic anion and is an anion corresponding to the acid (HX) to be generated by irradiating the sulfonium salt of the present invention with active energy rays (visible light, ultraviolet rays, electron beams, X-rays, or the like), is preferably an anion represented by $MY_a^-$, $(Rf)_b PF_{6-b}^-$, $R^7{}_c BY_{4-c}^-$, $R^7{}_c GaY_{4-c}^-$, $R^8 SO_3^-$, $(R^8 SO_2)_3 C^-$, or $(R^8 SO_2)_2 N^-$.

M represents a phosphorus atom, a boron atom, an arsenic atom, or an antimony atom.

Y represents a halogen atom (a fluorine atom is preferred).

Rf represents an alkyl group (an alkyl group having 1 to 8 carbon atoms is preferred) in which 80 mol % or more of hydrogen atoms are substituted with fluorine atoms. Examples of Rf include straight chain alkyl groups (methyl, ethyl, propyl, butyl, pentyl, octyl, and the like), branched alkyl groups (isopropyl, isobutyl, sec-butyl, tert-butyl, and the like), and cycloalkyl groups (cyclopropyl, cyclobutyl, cyclopentyl, cyclohexyl, and the like). The ratio at which the hydrogen atoms of these alkyl groups are substituted with fluorine atoms is preferably 80 mol % or more, more preferably 90 mol % or more, and particularly preferably 100 mol %, based on the molar number of all hydrogen atoms originally contained. When being within such ranges, the photosensitivity of a sulfonium salt becomes better. Particularly preferred members of Rf include $CF_3$—, $CF_3CF_2$—, $(CF_3)_2$ CF—, $CF_3CF_2CF_2$—, $CF_3CF_2CF_2CF_2$—, $(CF_3)_2 CFCF_2$—, $CF_3CF_2(CF_3)CF$—, and $(CF_3)_3 C$—. b-Rfs may be either the same or different.

P and F represent a phosphorus atom and a fluorine atom, respectively.

$R^7$ represents a phenyl group of which part of the hydrogen atoms is substituted with at least one element or an electron-accepting group. The one element includes a halogen atom, which includes a fluorine atom, a chlorine atom, and a bromine atom. Examples of the electron-accepting group include a trifluoromethyl group, a nitro group, and a cyano group. Preferred among these is a phenyl group of which one hydrogen atom is substituted with a fluorine atom or a trifluoromethyl group. c-$R^7$'s may be either the same or different.

B and Ga represent a boron atom and a gallium atom, respectively.

$R^8$ represents an alkyl group having 1 to 20 carbon atoms, a perfluoroalkyl group having 1 to 20 carbon atoms, or an aryl group having 6 to 20 carbon atoms, wherein the alkyl group and the perfluoroalkyl group each may be straight chain, branched, or cyclic, and the aryl group may either be unsubstituted or have a substituent.

S, O, C, and N represent a sulfur atom, an oxygen atom, a carbon atom, and a nitrogen atom, respectively.

a represents an integer of 4 to 6.

b is preferably an integer of 1 to 5, more preferably 2 to 4, and particularly preferably 2 or 3.

c is preferably an integer of 1 to 4, more preferably 4.

Examples of the anion represented by $MY_a^-$ include anions represented by $SbF_6^-$, $AsF_6^-$, $PF_6^-$, or $BF_4^-$.

Examples of the anion represented by $(Rf)_b PF_{6-b}^-$ include anions represented by $(CF_3CF_2)_2 PF_4^-$, $(CF_3CF_2)_3 PF_3^-$, $((CF_3)_2 CF)_2 PF_4^-$, $((CF_3)_2 CF)_3 PF_3^-$, $(CF_3CF_2CF_2)_2 PF_4^-$, $(CF_3CF_2CF_2)_3 PF_3^-$, $((CF_3)_2 CFCF_2)_2 PF_4^-$, $((CF_3)_2 CFCF_2)_3 PF_3^-$, $(CF_3CF_2CF_2CF_2)_2 PF_4^-$, or $(CF_3CF_2CF_2CF_2)_3 PF_3^-$. Preferred among these are anions represented by $(CF_3CF_2)_3 PF_3^-$, $(CF_3CF_2CF_2)_3 PF_3^-$, $((CF_3)_2 CF)_3 PF_3^-$, $((CF_3)_2 CF)_2 PF_4^-$, $((CF_3)_2 CFCF_2)_3 PF_3^-$, or $((CF_3)_2 CFCF_2)_2 PF_4^-$.

Examples of the anion represented by $R^7{}_c BY_{4-c}^-$ include anions represented by $(C_6F_5)_4 B^-$, $((CF_3)_2 C_6H_3)_4 B^-$, $(CF_3C_6H_4)_4 B^-$, $(C_6F_5)_2 BF_2^-$, $C_6F_5 BF_3^-$, or $(C_6H_3F_2)_4 B^-$. Preferred among these are anions represented by $(C_6F_5)_4 B^-$ or $((CF_3)_2 C_6H_3)_4 B^-$.

Examples of the anion represented by $R^7{}_c GaY_{4-c}^-$ include anions represented by $(C_6F_5)_4 Ga^-$, $((CF_3)_2 C_6H_3)_4 Ga^-$, $(CF_3C_6H_4)_4 Ga^-$, $(C_6F_5)_2 GaF_2^-$, $C_6F_5 GaF_3^-$, or $(C_6H_3F_2)_4 Ga^-$. Preferred among these are anions represented by $(C_6F_5)_4 Ga^-$ or $((CF_3)_2 C_6H_3)_4 Ga^-$.

Examples of the anion represented by $R^8 SO_3^-$ include a trifluoromethanesulfonate anion, a pentafluoroethanesulfonate anion, a heptafluoropropanesulfonate anion, a nonafluorobutanesulfonate anion, a pentafluorophenylsulfonate anion, a p-toluenesulfonate anion, a benzenesulfonate anion, a camphorsulfonate anion, a methanesulfonate anion, an ethanesulfonate anion, a propanesulfonate anion, and a butanesulfonate anion.

Examples of the anion represented by $(R^8 SO_2)_3 C^-$ include anions represented by $(CF_3 SO_2)_3 C^-$, $(C_2F_5 SO_2)_3 C^-$, $(C_3F_7 SO_2)_3 C^-$, or $(C_4F_3 SO_2)_3 C^-$.

Examples of the anion represented by $(R^8 SO_2)_2 N^-$ include anions represented by $(CF_3 SO_2)_2 N^-$, $(C_2F_5 SO_2)_2 N^-$, $(C_3F_7 SO_2)_2 N^-$, or $(C_4F_3 SO_2)_2 N^-$.

Besides anions represented by $MY_a^-$, $(Rf)_b PF_{6-b}^-$, $R^7{}_c BY_{4-c}^-$, $R^7{}_c GaY_{4-c}^-$, $R^8 SO_3^-$, $(R^8 SO_2)_3 C^-$, or $(R^8 SO_2)_2 N^-$, perhalogenic acid ions ($ClO_4^-$, $BrO_4^-$, and the like), halogenated sulfonate ions ($FSO_3^-$, $ClSO_3^-$, and the like), sulfate ions ($CH_3 SO_4^-$, $CF_3 SO_4^-$, $HSO_4^-$, and the like), carbonate ions ($HCO_3^-$, $CH_3 CO_3^-$, and the like), aluminate ions ($AlCl_4^-$, $AlF_4^-$, and the like), a hexafluorobismuthic acid ion ($BiF_6^-$), carboxylate ions ($CH_3 COO^-$, $CF_3 COO^-$, $C_6H_5 COO^-$, $CH_3 C_6H_4 COO^-$, $C_6F_5 COO^-$, $CF_3 C_6H_4 COO^-$, and the like), arylborate ions ($B(C_6H_5)_4^-$, $CH_3CH_2CH_2CH_2 B(C_6H_5)_3^-$, and the like), a thiocyanate ion ($SCN^-$), a nitrate ion ($NO_3^-$), and the like can be used as the monovalent polyatomic anion.

The sulfonium salt of the present invention can be produced by production methods (1) to (4) and the like.

<Production Method (1)>

A method represented by the following reaction formula (for example, the methods disclosed in "Jikken Kagaku Koza (Lectures of Experimental Chemistry)" 4th Edition, vol. 24, p. 376, published by Maruzen Co., Ltd. (1992), JP 7-329399 A, JP 8-165290 A, JP 10-212286 A or JP 10-7680 A (corresponding U.S. Pat. No. 6,054,501, which is incorporated herein by reference in its entirety).

[Chem. 4]

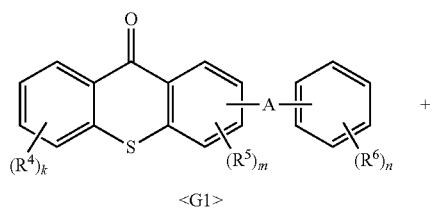

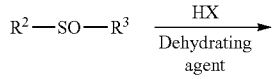

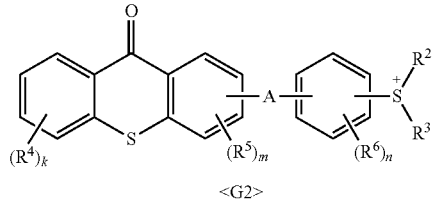

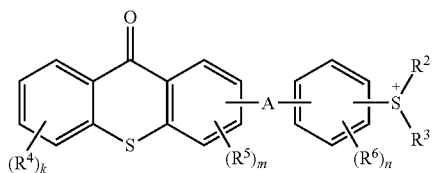

In the reaction formula, $R^2$, $R^3$, $R^4$, $R^5$, $R^6$, A, S, O, $X^-$, k, m, and n are the same as those in formulae (1) and (2).

HX represents a conjugate acid of a monovalent polyatomic anion. Methanesulfonic acid, perfluoromethanesulfonic acid, and sulfuric acid are preferred as HX from the viewpoints of availability, and the stability and the reaction yield of an acid.

The dehydrating agent represents, for example, phosphoric anhydride, acetic anhydride, and the like.

The monovalent polyatomic anion ($X^-$) can be exchanged for another monovalent polyatomic anions ($X^{l-}$) by, for example, a metathetical reaction as shown above.

MX' represents a salt of an alkali metal (lithium, sodium, potassium, or the like) cation with a monovalent polyatomic anion (anions represented by $MY_a^-$, $(Rf)_bPF_{6-b}^-$, $R^7_cBY_{4-c}^-$, $R^7_cGaY_{4-c}^-$, $R^8SO_3^-$, $(R^8SO_2)_3C^-$, or $(R^8SO_2)_2N^-$ are preferred).

MX represents a salt of an alkali metal (lithium, sodium, potassium, or the like) cation with a monovalent polyatomic anion (a methanesulfonate anion, a perfluoromethanesulfonate anion, and a hydrogen sulfate anion are preferred).

In the reaction formula provided above, the first step reaction may be performed in the absence of a solvent and also may be performed in an organic solvent (acetonitrile, tetrahydrofuran, dioxane, ethanol, acetone, or the like) as necessary The reaction temperature is approximately 20 to 105° C. The reaction time is approximately 1 to several tens of hours.

The second step reaction may be carried out succeedingly to the first step reaction and also may be carried out after isolating (as necessary, purifying) the reaction intermediate (G2). The sulfonium salt of the present invention is obtained in the form of a solid or a viscous liquid by mixing and stirring the reaction intermediate (G2) and an aqueous solution of the salt (MX) of an alkali metal cation with a monovalent polyatomic anion to perform a metathetical reaction, followed either by collecting a formed solid by filtration or by extracting a separated oil with an organic solvent and then removing the organic solvent. As necessary, the solid or viscous liquid obtained may be purified by washing with an appropriate organic solvent, recrystallization, or column chromatography (this is also applied hereafter).

<Production Method (2)>

A method represented by the following reaction formula (for example, the method described in Polymer Bulletin, 14, 279-286 (1985), which is incorporated herein by reference in its entirety).

[Chem. 5]

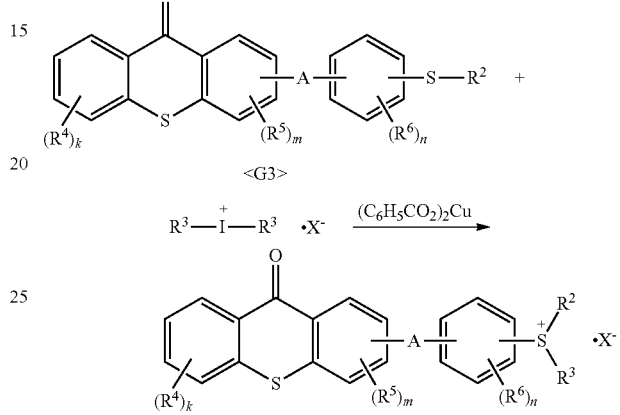

In the reaction formula, $R^2$, $R^3$, $R^4$, $R^5$, $R^6$, A, S, O, $X^-$, k, m, and n are the same as those in formulae (1) and (2).

I represents an iodine atom.

$(C_6H_5CO_2)_2Cu$ represents copper benzoate.

The reaction provided above can be performed in an organic solvent (chlorobenzene, nitrobenzene, or the like). Copper benzoate is used as a catalyst.

The reaction temperature is approximately 100 to 130° C. The reaction time is approximately 1 to several tens of hours.

The sulfonium salt of the present invention is obtained in the form of a solid or a viscous liquid by pouring the reaction solution into ether or the like after the completion of the reaction, followed either by collecting a formed solid by filtration or by extracting a separated oil with an organic solvent and then removing the solvent.

<Production Method (3)>

A method represented by the following reaction formula (for example, the method described in JP 7-300504 A (corresponding U.S. Pat. No. 5,798,396, which is incorporated herein by reference in its entirety).

[Chem. 6]

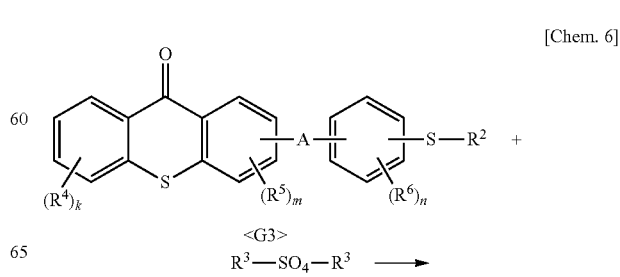

-continued

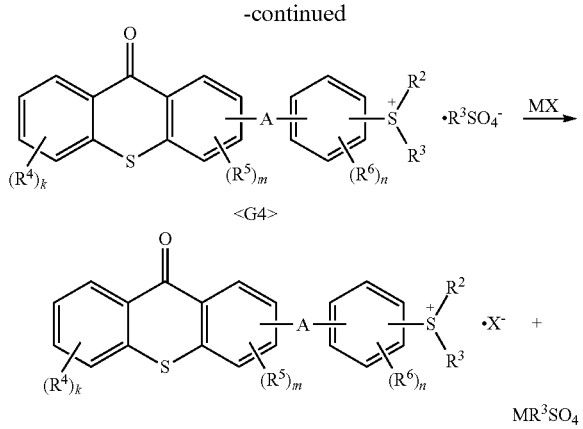

In the reaction formula, $R^2$, $R^3$, $R^4$, $R^5$, $R^6$, A, S, O, $X^-$, k, m, and n are the same as those in formulae (1) and (2).

MX is the same as that described above.

$R^3SO_4^-$ represents an organic sulfate anion.

$MR^3SO_4$ represents a salt of an alkali metal cation with an organic sulfate anion.

In the reaction formula provided above, the first step reaction may be performed in the absence of a solvent and also may be performed in an organic solvent (acetonitrile, ethyl acetate, tetrahydrofuran, dioxane, ethanol, acetone, methyl ethyl ketone, chloroform, dichloromethane, or the like) as necessary The reaction temperature is approximately 20 to 105° C. The reaction time is approximately 1 to several tens of hours.

The second step reaction can be performed in the same manner as in Production method (1).

<Production Method (4)>

A method represented by the following reaction formula.

[Chem. 7]

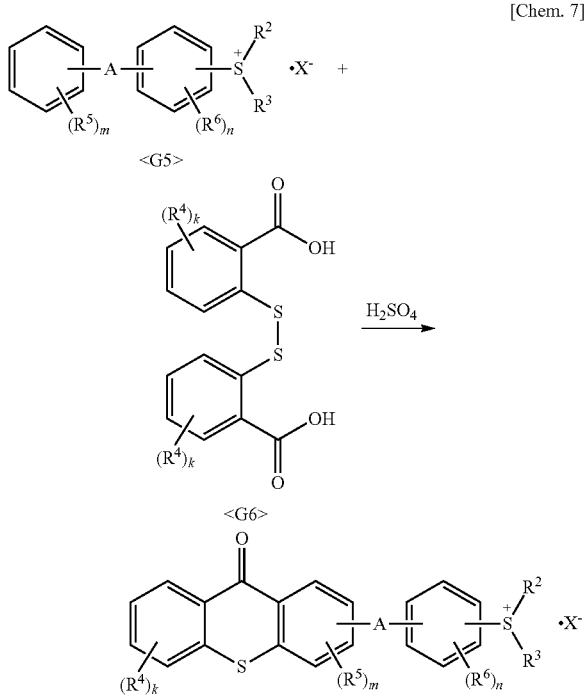

In the reaction formula, $R^2$, $R^3$, $R^4$, $R^5$, $R^6$, A, S, O, $X^-$, k, m, and n are the same as those in formulae (1) and (2).

H represents a hydrogen atom.

$H_2SO_4$ represents sulfuric acid.

The reaction shown above may be carried out in the absence of a solvent or may be performed in an organic solvent as necessary. The reaction temperature is preferably approximately from 20 to 100° C., more preferably from 20 to 30° C. The reaction time is preferably approximately from 1 to several tens of hours, more preferably from 1 to 3 hours. The sulfonium salt of the present invention is obtained in the form of a solid or a viscous liquid by pouring the reaction solution into water (distilled water, or the like) after the completion of the reaction, followed either by collecting a formed solid by filtration or by extracting a separated oil with an organic solvent and then removing the solvent.

The used amount (% by weight) of sulfuric acid is preferably approximately from 2000 to 4000, and is more preferably from 2500 to 3500, based on the weight of disulfide (G6).

The used amount (% by weight) of water is preferably approximately from 20000 to 40000, and is more preferably from 25000 to 35000, based on the weight of disulfide (G6).

The raw material (G1) to be used in the production method described above can be obtained by known methods and can be produced, for example, according to Reaction formulae (1) through (4) shown below.

<Reaction Formula (1)>

[Chem. 8]

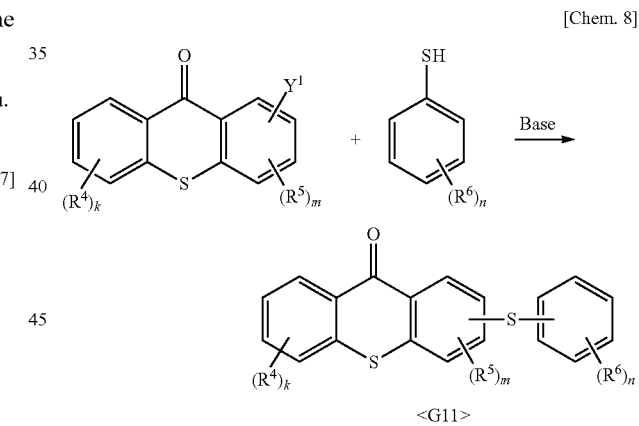

In the reaction formula, $R^4$, $R^5$, $R^6$, S, O, k, m, and n are the same as those in formula (2).

$Y^1$ represents a chlorine atom or a bromine atom.

H represents a hydrogen atom.

Base represents a base (potassium hydroxide, or the like).

A sulfide (G11) having a thioxanthone skeleton is obtained by making a thioxanthone derivative and a thiophenol derivative react together in the presence of a base in an organic solvent (dimethylformamide, or the like).

<Reaction Formula (2)>

To Reaction formula (2) can be applied the oxidation reaction described in "Jikken Kagaku Koza (Lectures of Experimental Chemistry)" 4th Edition, vol. 23, pp. 276-277 (1991, Maruzen Co., Ltd.).

[Chem. 9]

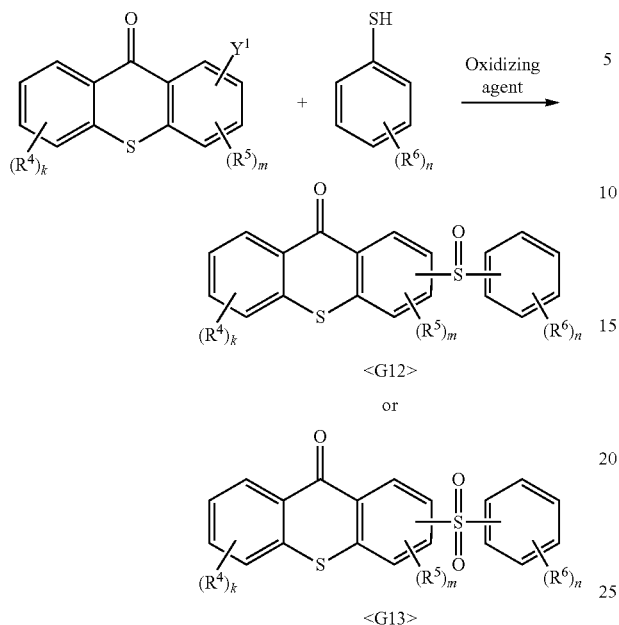

\<G12\> or

\<G13\>

In the reaction formula, $R^4$, $R^5$, $R^6$, S, O, k, m, and n are the same as those in formula (2).

H represents a hydrogen atom.

Oxidizing agent represents an oxidizing agent (hydrogen peroxide, or the like).

A sulfoxide (G12) having a thioxanthone skeleton is obtained by oxidizing a sulfide (G11) having a thioxanthone skeleton by using an oxidizing agent under mild conditions. If oxidation is carried out in the presence of an excess oxidizing agent under strong conditions, the sulfide (G11) is further oxidized, so that a sulfone (G13) having a thioxanthone skeleton is obtained.

\<Reaction Formula (3)\>

[Chem. 10]

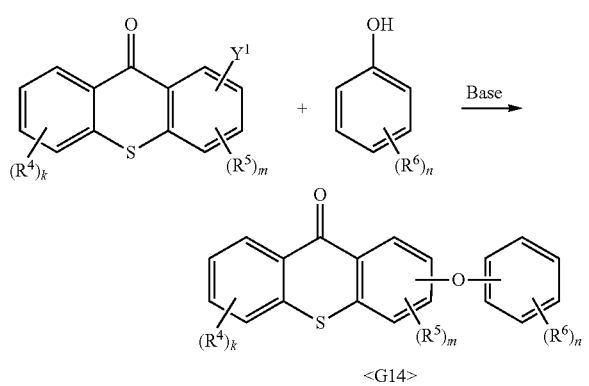

\<G14\>

In the reaction formula, $R^4$, $R^5$, $R^6$, S, O, k, m, and n are the same as those in formula (2).

$Y^1$ represents a chlorine atom or a bromine atom.

H represents a hydrogen atom.

Base represents a base (potassium hydroxide, or the like).

An ether having a thioxanthone skeleton is obtained by making a thioxanthone derivative and a phenol derivative react together in the presence of a base in an organic solvent (dimethylformamide, or the like).

\<Reaction Formula (4)\>

To the first step reaction of the following Reaction formula (4) can be applied the reaction described in "Jikken Kagaku Koza (Lectures of Experimental Chemistry)" 4th Edition, vol. 19, p. 424 (1992, Maruzen Co., Ltd.).

To the second step reaction can be applied the reaction described in "Shin Jikken Kagaku Koza (New Lectures of Experimental Chemistry)", vol. 14-II, p. 804 (1978, Maruzen Co., Ltd.).

[Chem. 11]

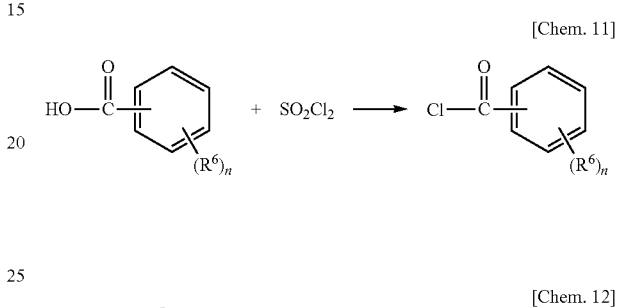

[Chem. 12]

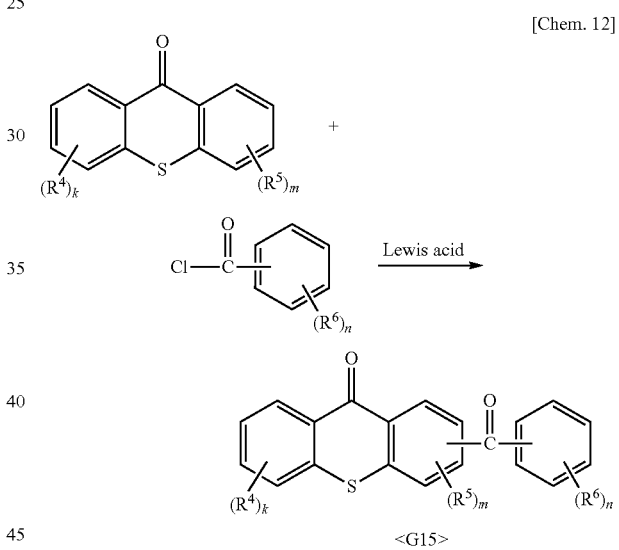

\<G15\>

In the reaction formula, $R^4$, $R^5$, $R^6$, S, O, k, m, and n are the same as those in formula (2).

H, Cl, and $SO_2Cl_2$ represent a hydrogen atom, a chlorine atom, and sulfuryl chloride, respectively.

Lewis acid represents, for example, a compound represented by $AlCl_3$, $SbCl_5$, or $FeCl_3$.

A halide of a benzoic acid derivative can be obtained by making the benzoic acid derivative and sulfuryl chloride ($SO_2Cl_2$) react together (the first step reaction). By subsequently making a thioxanthone derivative and the halide of the benzoic acid derivative react together in the presence of a Lewis acid, a ketone having a thioxanthone skeleton is obtained (second step reaction).

The raw material (G3) to be used in the production method described above can be obtained by known methods and can be produced, for example, according to Reaction formula (5) shown below.

<Reaction Formula (5)>

[Chem. 13]

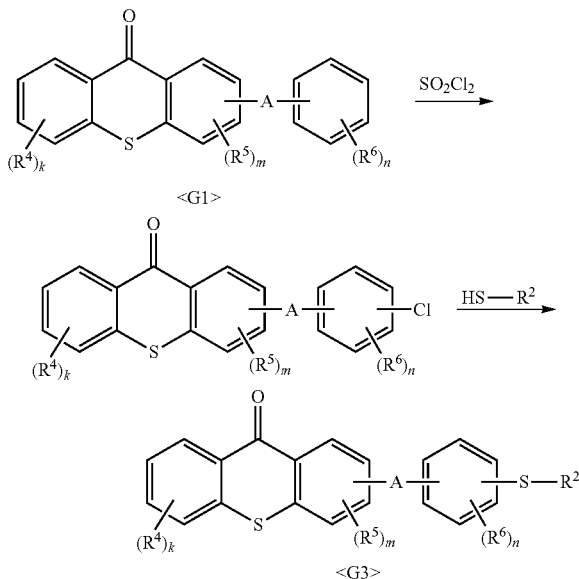

In the reaction formula, $R^4$, $R^5$, $R^6$, S, O, k, m, and n are the same as those in formula (2).

$SO_2Cl_2$ represents sulfuryl chloride.

HS—$R^2$ represents a thiol.

A sulfide (G3) having a thioxanthone skeleton is obtained by chlorinating a thioxanthone derivative (obtained in the same manner as reaction formulas (1) through (4)) with sulfuryl chloride (first step reaction) and then making the resulting chlorinated product of the thioxanthone derivative and a thiol react together in the presence of a base in an organic solvent (dimethylformamide, or the like).

The raw material (G5) to be used in the production method described above can be obtained by known methods and can be produced, for example, according to Reaction formula (6) shown below.

<Reaction Formula (6)>

A method similar to Production method (1) can be applied.

[Chem. 14]

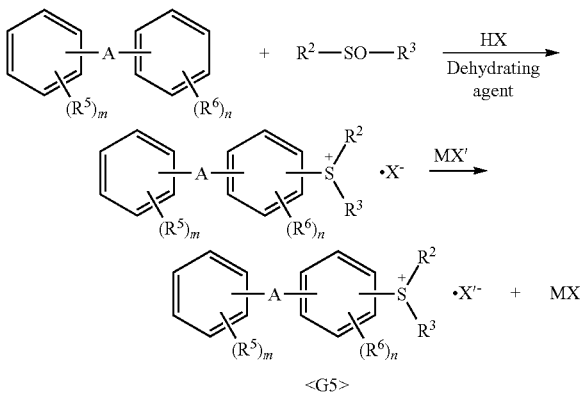

In the reaction formula, $R^4$, $R^5$, $R^6$, S, O, k, m, and n are the same as those in formula (2).

HX represents a strong acid (for example, methanesulfonic acid, perfluoromethanesulfonic acid, or sulfuric acid).

The dehydrating agent represents, for example, phosphoric anhydride, acetic anhydride, or the like.

In the reaction formula, $R^2$, $R^3$, $R^4$, $R^5$, $R^6$, A, S, O, $X^-$, k, m, and n are the same as those in formulae (1) and (2).

HX represents a conjugate acid of a monovalent polyatomic anion. Methanesulfonic acid, perfluoromethanesulfonic acid, and sulfuric acid are preferred as HX from the viewpoints of availability, and the stability and the reaction yield of an acid.

Dehydrating agent represents, for example, phosphoric anhydride, acetic anhydride, or the like.

The monovalent polyatomic anion ($X^-$) can be exchanged for another monovalent polyatomic anion ($X'^-$) by, for example, a metathetical reaction as shown above.

MX' represents a salt of an alkali metal (lithium, sodium, potassium, or the like) cation with a monovalent polyatomic anion (an anion represented by $MY_a^-$, $(Rf)_bPF_6^-$, $R^7_cBY_{4-c}^-$, $R^7_cGaY_{4-c}^-$, $R^8SO_3^-$, $(R^8SO_2)_3C^-$, or $(R^8SO_2)_2N^-$ is preferred).

MX represents a salt of an alkali metal (lithium, sodium, potassium, or the like) cation with a monovalent polyatomic anion (a methanesulfonate anion, a perfluoromethanesulfonate anion, and a sulfate anion are preferred).

A sulfonium salt (G5) can be obtained from diphenylsulfide, diphenyl sulfoxide, diphenyl sulfone, diphenyl ether or benzophenone and diphenylsulfide in the same manner as in Production method (1).

The chemical structure of the sulfonium salt of the present invention can be identified by a common analysis method (for example, $^1$H-, $^{11}$B-, $^{13}$C-, $^{19}$F-, $^{31}$P-nuclear magnetic resonance spectrum, infrared absorption spectrum, and/or elemental analysis, or the like).

The sulfonium salt of the present invention is suitable as a photoacid generator.

The photoacid generator refers to a substance whose chemical structure is decomposed by exposure to light to generate an acid. The generated acid can be applied as a catalyst for, for example, a curing reaction of an epoxide.

The photoacid generator of the present invention may be used alone and also may contain an additional photoacid generator.

When the photoacid generator of the present invention contains an additional photoacid generator, the content (mol %) of the additional photoacid generator is preferably 1 to 100 and is more preferably 5 to 50, based on the molar number of the sulfonium salt.

Examples of the additional photoacid generator include a salt of an onium ion (sulfonium, iodonium, selenium, ammonium, phosphonium, or the like) or a transition metal complex ion with an anion.

Besides anions represented by $MY_a^-$, $(Rf)_bPF_{6-b}^-$, $R^7_cBY_{4-c}^-$, $R^7_cGaY_{4-c}^-$, $R^8SO_3^-$, $(R^8SO_2)_3C^-$, or $(R^8SO_2)_2N^-$, perhalogenic acid ions ($ClO_4^-$, $BrO_4^-$, and the like), halogenated sulfonate ions ($FSO_3^-$, $ClSO_3^-$, and the like), sulfate ions ($CH_3SO_4^-$, $CF_3SO_4^-$, $HSO_4^-$, and the like), carbonate ions ($HCO_3^-$, $CH_3CO_3^-$, and the like), aluminate ions ($AlCl_4^-$, $AlF_4^-$, and the like), a hexafluorobismuthic acid ion ($BiF_6^-$), carboxylate ions ($CH_3COO^-$, $CF_3COO^-$, $C_6H_5COO^-$, $CH_3C_6H_4COO^-$, $C_6F_5COO^-$, $CF_3C_6H_4COO^-$, and the like), arylborate ions ($B(C_6H_5)_4^-$, $CH_3CH_2CH_2CH_2B(C_6H_5)_3^-$, and the like), a thiocyanate ion ($SCN^-$), a nitrate ion ($NO_3^-$), and the like can be used as the anion.

Examples of the sulfonium ion include triarylsulfonium, diarylsulfonium, monoarylsulfonium, and trialkylsulfonium.

Examples of the triarylsulfonium include triphenylsulfonium, tri-p-tolyl sulfonium, tri-o-tolyl sulfonium, tris(4-methoxyphenyl)sulfonium, 1-naphthyldiphenylsulfonium, 2-naphthyldiphenylsulfonium, tris(4-fluorophenyl)sulfonium, tri-1-naphthylsulfonium, tri-2-naphthylsulfonium, tris (4-hydroxyphenyl)sulfonium, 4-(phenylthio)phenyldiphenylsulfonium, 4-(p-tolylthio)phenyldi-p-tolylsulfonium, 4-(4-methoxyphenylthio)phenylbis(4-methoxyphenyl)sulfonium, 4-(phenylthio)phenylbis(4-fluorophenyl)sulfonium, 4-(phenylthio)phenylbis(4-methoxyphenyl)sulfonium, 4-(phenylthio)phenyldi-p-tolylsulfonium, bis[4-(diphenylsulfonio)phenyl]sulfide, bis[4-{bis[4-(2-hydroxyethoxy)phenyl]sulfonio}phenyl]sulfide, bis{4-[bis(4-fluorophenyl)sulfonio]phenyl}sulfide, bis{4-[bis(4-methylphenyl)sulfonio]phenyl}sulfide, bis{4-[bis(4-methoxyphenyl)sulfonio]phenyl}sulfide, 4-(4-benzoyl-2-chlorophenylthio)phenylbis(4-fluorophenyl)sulfonium, 4-(4-benzoyl-2-chlorophenylthio)phenyldiphenylsulfonium, 4-(4-benzoylphenylthio)phenylbis(4-fluorophenyl)sulfonium, 4-(4-benzoylphenylthio)phenyldiphenylsulfonium, 7-isopropyl-9-oxo-10-thia-9,10-dihydroanthracen-2-yldi-p-tolylsulfonium, 7-isopropyl-9-oxo-10-thia-9,10-dihydroanthracen-2-yldiphenylsulfonium, 2-[(di-p-tolyl)sulfonio]thioxanthone, 2-[(diphenyl)sulfonio]thioxanthone, 2-{[4-(phenylthio)phenyl]phenylsulfonio}thioxanthone, 4-[4-(4-tert-butylbenzoyl)phenylthio]phenyldi-p-tolylsulfonium, 4-[4-(4-tert-butylbenzoyl)phenylthio]phenyldiphenylsulfonium, 4-[4-(benzoylphenylthio)]phenyldi-p-tolylsulfonium, 4-[4-(benzoylphenylthio)]phenyldiphenylsulfonium, 5-(4-methoxyphenyl)thianthrenium, 5-phenylthianthrenium, 5-tolylthianthrenium, 5-(4-ethoxyphenyl)thianthrenium, and 5-(2,4,6-trimethylphenyl)thianthrenium, (U.S. Pat. No. 4,231,951, U.S. Pat. No. 4,256,828, and JP 7-61964 A (corresponding U.S. Pat. Nos. 5,502,083 and 5,534,557), JP 7-10914 A, JP 7-25922 A, JP 8-27208 A, JP 8-27209 A, JP 8-165290 A, JP 8-301991 A, JP 9-143212 A, JP 9-278813 A, JP 10-7680 A (corresponding U.S. Pat. No. 6,054,501), JP 10-212286 A, JP 10-287643 A, JP 10-245378 A, JP 8-157510 A, JP 10-204083 A, JP 8-245566 A, JP 8-157451 A, JP 7-324069 A (corresponding U.S. Pat. Nos. 5,633,409 and 5,691,112), JP 9-268205 A, JP 9-278935 A, JP 2001-288205 A, JP 11-80118 A, JP 10-182825 A, JP 10-330353 A, JP 10-152495 A, JP 5-239213 A, JP 7-333834 A (corresponding U.S. Pat. No. 5,624,787), JP 9-12537 A, JP 8-325259 A, JP 8-160606 A (corresponding U.S. Pat. No. 5,679,496), JP 2000-186071 A (corresponding U.S. Pat. No. 6,368,769), JP 2005-501040 T (corresponding PCT pamphlet WO03/008404), JP 2005-530698 A (corresponding PCT pamphlet WO03/072568), JP 2006-104185 A (corresponding U.S. Pat. Appl. Nos. 2004/0244641 and 2007/0054974), JP 2006-518332 T (corresponding PCT pamphlet WO2004/055000), JP 2007-254454 A (corresponding U.S. Pat Appl. No. 2007/0197677), and the like; these documents are incorporated herein by reference in their entirety).

Examples of the diaryl sulfonium include diphenylphenacylsulfonium, diphenyl-4-nitrophenacylsulfonium, diphenylbenzylsulfonium, and diphenylmethyl sulfonium (JP 7-300504 A (corresponding U.S. Pat. No. 5,798,396), JP 64-45357 A, JP 64-29419 A, and the like; these documents are incorporated herein by reference in their entirety).

Examples of the monoarylsulfonium include phenylmethylbenzylsulfonium, 4-hydroxyphenylmethylbenzylsulfonium, 4-methoxyphenylmethylbenzylsulfonium, 4-acetocarbonyloxyphenylmethylbenzylsulfonium, 2-naphthylmethylbenzylsulfonium, 2-naphthylmethyl(1-ethoxycarbonyl)ethylsulfonium, phenylmethylphenacylsulfonium, 4-hydroxyphenylmethylphenacylsulfonium, 4-methoxyphenylmethylphenacylsulfonium, 4-acetocarbonyloxyphenylmethylphenacylsulfonium, 2-naphthylmethylphenacylsulfonium, 2-naphthyloctadecylphenacylsulfonium, and 9-anthracenylmethylphenacylsulfonium (JP 6-345726 A, JP 8-325225 A, JP 9-118663 A (corresponding U.S. Pat. No. 6,093,753), JP 2-196812 A (corresponding U.S. Pat. No. 5,399,596), JP 2-1470 A (corresponding U.S. Pat. No. 5,399,596), JP 2-196812 A (corresponding U.S. Pat. No. 5,399,596), JP 3-237107 A, JP 3-17101 A, JP 6-228086 A, JP 10-152469 A, JP 7-300505 A (corresponding U.S. Pat. No. 5,798,396), JP 2000-39706 A (corresponding PCT pamphlet WO91/06039), JP 2003-277353 A, JP 2003-277352 A, and the like; these documents are incorporated herein by reference in their entirety).

Examples of the trialkyl sulfonium include dimethylphenacylsulfonium, phenacyltetrahydrothiophenium, dimethylbenzylsulfonium, benzyltetrahydrothiophenium, and octadecylmethylphenacylsulfonium (JP 4-308563 A, JP 5-140210 A, JP 5-140209 A, JP 5-230189 A, JP 6-271532 A, JP 58-37003 A, JP 2-178303 A, JP 10-338688 A, JP 9-328506 A, JP 11-228534 A, JP 8-27102 A (corresponding U.S. Pat. Nos. 5,691,111 and 5,756,850), JP 7-333834 A (corresponding U.S. Pat. No. 5,624,787), JP 5-222167 A (corresponding European Patent No. 0527107 B1), JP 11-21307 A (corresponding U.S. Pat. No. 6,127,092), JP 11-35613 A (corresponding U.S. Pat. No. 6,162,881), U.S. Pat. No. 6,031,014, and the like; these documents are incorporated herein by reference in their entirety).

Examples of the iodonium ion include diphenyliodonium, di-p-tolyliodonium, bis(4-dodecylphenyl)iodonium, bis(4-methoxyphenyl)iodonium, (4-octyloxyphenyl)phenyliodonium, bis(4-decyloxyphenyl)iodonium, 4-(2-hydroxytetradecyloxy)phenylphenyliodonium, 4-isopropylphenyl(p-tolyl)iodonium, and isobutylphenyl(p-tolyl)iodonium (Macromolecules, 10, 1307 (1977), JP 6-184170 A (corresponding U.S. Pat. Nos. 5,468,902, 5,550,265, 5,668,192, 6,147,184, and 6,153,661), U.S. Pat. No. 4,256,828, U.S. Pat. No. 4,351,708, JP 56-135519 A (corresponding U.S. Pat. No. 4,351,708), JP 58-38350 A, JP 10-195117 A, JP 2001-139539 A (corresponding U.S. Pat. No. 6,380,277), JP 2000-510516 A (corresponding U.S. Pat. No. 6,291,540), JP 2000-119306 A (corresponding European Patent No. 0994124 B1), and the like; these documents are incorporated herein by reference in their entirety).

Examples of the selenium ion include triarylseleniums (triphenylselenium, tri-p-tolylselenium, tri-o-tolylselenium, tris(4-methoxyphenyl)selenium, 1-naphthyldiphenylselenium, tris(4-fluorophenyl)selenium, tri-1-naphthylselenium, tri-2-naphthylselenium, tris(4-hydroxyphenyl)selenium, 4-(phenylthio)phenyldiphenylselenium, 4-(p-tolylthio)phenyldi-p-tolylselenium, and the like), diarylseleniums (diphenylphenacylselenium, diphenylbenzylselenium, diphenylmethylselenium, and the like), monoarylseleniums (phenylmethylbenzylselenium, 4-hydroxyphenylmethylbenzylselenium, phenylmethylphenacylselenium, 4-hydroxyphenylmethylphenacylselenium, 4-methoxyphenylmethylphenacylselenium, and the like), and trialkylseleniums (dimethylphenacylselenium, phenacyltetrahydroselenophenium, dimethylbenzylselenium, benzyltetrahydroselenophenium, octadecylmethylphenacylselenium, and the like) (JP 50-151997 A (corresponding U.S. Pat. Nos. 4,058,401, 4,136,102, 4,161,478, 4,173,551, 4,175,972, 4,219,654, 4,234,732, 4,250,311, 4,273,668, 4,283,312, 4,407,759, and 4,417,061), JP 50-151976 A (corresponding U.S. Pat. Nos. 4,058,400 and 4,161,405), JP 53-22597 A (corresponding U.S. Pat. No. 4,193,799), and the like; these documents are incorporated herein by reference in their entirety).

Examples of the ammonium ion include tetraalkylammoniums (tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, trimethylisobutylammonium, trimethyl-tert-butylammonium, trimethyl-n-hexylammonium, dimethyldi-n-propylammonium, dimethyldiisopropylammonium, dimethyl-n-propylisopropylammonium, methyltri-n-propylammonium, methyltriisopropylammonium, and the like), pyrrolidiniums (N,N-dimethylpyrrolidinium, N-ethyl-N-methylpyrrolidinium, N,N-diethylpyrroliclinium, and the like), imidazoliniums N,N'-diethylimidazolinium, N-ethyl-N'-methylimidazolinium, 1,2,3-trimethylimidazolinium, 1,3,4-trimethylimidazolinium, 1,3-diethyl-2-methylimidazolinium, 1,3-diethyl-4-methylimidazolinium, 1,2,3,4-tetramethylimidazolinium, and the like), tetrahydropyrimidiniums (N,N'-dimethyltetrahydropyrimidinium, N,N'-diethyltetrahydropyrimidinium, N-ethyl-N'-methyltetrahydropyrimidinium, 1,2,3-trimethyltetrahydropyrimidinium, and the like), morpholiniums (N,N'-dimethylmorpholinium, N-ethyl-N-methylmorpholinium, N,N-diethylmorpholinium, and the like), piperidiniums (N,N-dimethylpiperidinium, N-ethyl-N'-methylpiperidinium, N,N'-diethylpiperidinium, and the like), pyridiniums (N-methylpyriclinium, N-ethylpyridinium, N-n-propylpyrklinium, Nisopropylpyrklinium, N-n-butylpyridinium, N-benzylpyridinium, N-phenacylpyridium, and the like), imidazoliums N-ethyl-N-methylimidazolium, N,N'-diethylimidazolium, 1,2-diethyl-3-methylimidazolium, 1,3-diethyl-2-methylimidazolium, 1-methyl-3-n-propyl-2,4-dimethylimidazolium, and the like), quinoliniums (N-methylquinolinium, N-ethylquinolinium, N-n-propylquinolinium, N-isopropylquinolinium, N-n-butylquinolinium, N-benzylquinolinium, N-phenacylquinolinium, and the like), isoquinoliniums (N-methylisoquinolinium, N-ethylisoquinolinium, N-n-propylisoquinolinium, N-isopropylisoquinolinium, N-n-butylisoquinolinium, N-benzylisoquinolinium, N-phenacylisoquinolinium, and the like), thiazoniums (benzylbenzothiazonium, phenacylbenzothiazonium, and the like), and acrydiums (benzylacrydium, phenacylacryclium, and the like) (U.S. Pat. No. 4,069,055, Japanese Patent No. 2519480, JP 5-222112 A, JP 5-222111 A, JP 5-262813 A, JP 5-255256 A, JP 7-109303 A, JP 10-101718 A, JP 2-268173 A, JP 9-328507 A, JP 5-132461 A, JP 9-221652 A, JP 7-43854 A, JP 7-43901 A, JP 5-262813 A, JP 4-327574 A, JP 2-43202 A, JP 60-203628 A, JP 57-209931 A (corresponding GB Patent Application No. 2099825), JP 9-221652 A, and the like; these documents are incorporated herein by reference in their entirety).

Examples of the phosphonium ion include tetraarylphosphoniums (tetraphenylphosphonium, tetra-p-tolylphosphonium, tetrakis(2-methoxyphenyl)phosphonium, tetrakis(3-methoxyphenyl)phosphonium, tetrakis(4-methoxyphenyl)phosphonium, and the like), triarylphosphoniums (triphenylbenzylphosphonium, triphenylphenacylphosphonium, triphenylmethylphosphonium, triphenylbutylphosphonium, and the like), and tetraalkylphosphoniums (triethylbenzylphosphonium, tributylbenzylphosphonium, tetraethylphosphonium, tetrabuthylphosphonium, tetrahexylphosphonium, triethylphenacylphosphonium, tributylphenacylphosphonium, and the like) (JP 6-157624 A, JP 5-105692 A, JP 7-82283 A, JP 9-202873 A, and the like).

Examples of the transition metal complex ion include chromium complex cations {(η5-cyclopentadienyl)(η6-toluene) Cr$^+$, (η5-cyclopentathenyl)(η6-xylene) Cr$^+$, (η5-cyclopentadienyl)(η6-1-methylnaphthalene) Cr$^+$, (η5-cyclopentadienyl)(η6-cumene) Cr$^+$, (η5-cyclopentadienyl)(η6-mesitylene) Cr$^+$, (η5-cyclopentadienyl)(η6-pyrene) Cr$^+$, (η5-fluorenyl)(η6-cumene) Cr$^+$, (η5-indenyl)(η6-cumene) Cr$^+$, bis(η6-mesitylene) Cr$^{2+}$, bis(η6-xylene) Cr$^{2+}$, bis(η6-cumene) Cr$^{2+}$, bis(η6-toluene) Cr$^{2+}$, (η6-toluene)(η6-xylene) Cr$^{2+}$, (η6-cumene)(η6-naphthalene) Cr$^{2+}$, bis(η5-cyclopentadienyl) Cr$^+$, bis(η5-indenyl) Cr$^+$, (η5-cyclopentadienyl)(η5-fluorenyl) Cr$^+$, (η5-cyclopentadienyl)(η5-indenyl) Cr$^+$, and the like}, and iron complex cations {(η5-cyclopentadienyl)(η6-toluene) Fe$^+$, (η5-cyclopentadienyl)(η6-xylene) Fe$^+$, (η5-cyclopentadienyl)(η6-1-methylnaphthalene) Fe$^+$, (η5-cyclopentadienyl)(η6-cumene) Fe$^+$, (η5-cyclopentadienyl)(η6-mesitylene) Fe$^+$, (η5-cyclopentadienyl)(η6-pyrene) Fe$^+$, (η5-fluorenyl)(η6-cumene) Fe$^+$, (η5-indenyl)(η6-cumene) Fe$^+$, bis(η6-mesitylene) Fe$^{2+}$, bis(η6-xylene) Fe$^{2+}$, bis(η6-cumene) Fe$^{2+}$, bis(η6-toluene) Fe$^{2+}$, (η6-toluene)(η6-xylene) Fe$^{2+}$, (η6-cumene)(η6-naphthalene) Fe$^{2+}$, bis(η5-cyclopentadienyl) Fe$^+$, bis(η5-indenyl) Fe$^+$, (η5-cyclopentadienyl)(η5-fluorenyl) Fe$^+$, (η5-cyclopentadienyl)(η5-indenyl) Fe$^+$, and the like} (Cr represents a chromium atom and Fe represents an iron atom) (Macromol. Chem., 81, 86 (1965), Angew. Makromol. Chem., 50, 9 (1976), Macromol. Chem., 153, 229 (1972), J. Polym. Sci., Polym. Chem. Edn., 14, 1547 (1976), Chem. Ztg., 108, 345 (1984), J. Imaging. Sci., 30, 174 (1986), J. Photochem. Photobiol. A: Chem., 77 (1994), J. Rad. Curing., 26 (1986), Adv. Polym. Sci., 78, 61 (1986), U.S. Pat. Nos. 4,973,722, 4,992,572, and 3,895,954, European Unexamined Patent Publication Nos. 203829, 354181, 94914, 109851, and 94915, JP 58-210904 A (corresponding U.S. Pat. No. 4,868,288), JP 59-108003 A (corresponding U.S. Pat. Nos. 5,089,536, 5,191,101, and 5,385,954), JP 2000-226396 A (corresponding European Patent No. 1153905), JP 2-284903 A (corresponding U.S. Pat. Nos. 5,130,406, 5,179,179, and 5,366,947), and the like; these documents are incorporated herein by reference in their entirety).

The photoacid generator of the present invention may be dissolved beforehand in a solvent that does not inhibit cationic polymerization in order to make its dissolution in a cationically polymerizable compound easier.

Examples of the solvent include carbonates (propylene carbonate, ethylene carbonate, 1,2-butylene carbonate, dimethyl carbonate, diethyl carbonate, and the like); esters (ethyl acetate, ethyl lactate, β-propiolactone, β-butyrolactone, γ-butyrolactone, δ-valerolactone, ε-caprolactone, and the like); ethers (ethylene glycol monomethyl ether, propylene glycol monoethyl ether, diethylene glycol monobutyl ether, dipropylene glycol dimethyl ether, triethylene glycol diethyl ether, tripropylene glycol dibutyl ether, and the like); and ether esters (ethylene glycol monomethyl ether acetate, propylene glycol monoethyl ether acetate, diethylene glycol monobutyl ether acetate, and the like).

When a solvent is used, the used amount of the solvent is preferably 15 to 1000 parts by weight and is more preferably 30 to 500 parts by weight relative to 100 parts by weight of the photoacid generator of the present invention.

The energy ray-curable composition of the present invention is composed of the above-mentioned photoacid generator and the above-mentioned cationically polymerizable compound.

Examples of the cationically polymerizable compound include cyclic ethers (epoxide, oxetane, and the like), ethylenically unsaturated compounds (vinyl ether, styrene, and the like), bicycloorthoester, spiroorthocarbonate, and spiroorthoester (JP 11-060996 A, JP 09-302269 A, JP 2003-026993 A, JP 2002-206017 A (corresponding U.S. Pat. Appl. No. 2003/0170396), JP 11-349895 A (corresponding U.S.

Pat. No. 6,322,892), JP 10-212343 A, JP 2000-119306 A (corresponding U.S. Pat. No. 6,558,871), JP 10-67812 A (corresponding U.S. Pat. No. 6,054,501), JP 2000-186071 A (corresponding U.S. Pat. No. 6,368,769), JP 08-85775 A, JP 08-134405 A, JP 2008-20838 A, JP 2008-20839 A, JP 2008-20841 A, JP 2008-26660 A, JP 2008-26644 A, JP 2007-277327 A, "Photopolymer Handbook" edited by The Technical Association of Photopolymers, Japan (1989, Kogyo Chosakai Publishing, Inc.), "Technology of UV/EB Curing", edited by Sogo Gijutsu Center (1982, Sogo Gijutsu Center), "UV/EB Curable Materials", edited by RadTech (1992, CMC), "Causes of UV Curing Defects/Inhibition and Remedies Therefor", edited by Technical Information Institute (2003, Technical Information Institute), Japan Society of Color Materials, 68, (5), 286-293 (1995), Fine Chemical, 29, (19), 5-14 (2000), and the like; these documents are incorporated herein by reference in their entirety).

As the epoxide can be used known substances, which include aromatic epoxides, alicyclic epoxides, and aliphatic epoxides.

Examples of the aromatic epoxides include glycidyl ethers of monohydric or polyhydric phenols having at least one aromatic ring (phenol, biphenol, bisphenol A, bisphenol F, phenol novolak, cresol novolak, their brominated products or their alkylene oxide adducts), and glycidyl esters (diglycidyl phthalate, diglycidyl-3-methylphthalate, and the like) of mono- or polycarboxylic acids having at least one aromatic ring (phthalic acid, 3-methylphthalic acid, and the like).

Examples of the alicyclic epoxides include compounds obtained by epoxydizing compounds having at least one cyclohexene ring or cyclopentene ring with an oxidizing agent [3,4-epoxycyclohexylmethyl-3,4-epoxycyclohexanecarboxylate, 3,4-epoxy-1-methylcyclohexyl-3,4-epoxy-1-methylhexanecarboxylate, 6-methyl-3,4-epoxycyclohexylmethyl-6-methyl-3,4-epoxycyclohexanecarboxylate, 3,4-epoxy-3-methylcyclohexylmethyl-3,4-epoxy-3-methylcyclohexanecarboxylate, 3,4-epoxy-5-methylcyclohexylmethyl-3,4-epoxy-5-methylcyclohexanecarboxylate, 2-(3,4-epoxycyclohexyl-5,5-spiro-3,4-epoxy)cyclohexanemetaclioxane, bis(3,4-epoxycyclohexylmethyl) adipate, 3,4-epoxy-6-methylcyclohexyl carboxylate, methylenebis(3,4-epoxycyclohexane), dicyclopentadiene diepoxide, ethylenebis(3,4-epoxycyclohexanecarboxylate), and the like].

Examples of the aliphatic epoxides include polyglycidyl ethers of aliphatic polyhydric alcohols or their alkylene oxide adducts (1,4-butanediol diglycidyl ether, 1,6-hexanediol diglycidyl ether, hydrogenated bisphenol A diglycidyl ether, triglycidyl ether of glycerol, triglycidyl ether of trimethylolpropane, tetraglycidyl ether of sorbitol, hexaglycidyl ether of dipentaerythritol, and the like), polyglycidyl esters of aliphatic polybasic acids (diglycidyl tetrahydrophthalate, diglycidyl hexahydrophthalate, diglycidyl hexahydro-3-methylphthalate, and the like), epoxydized products of long chain unsaturated compounds (epoxidized soybean oil, epoxidized polybutadiene, and the like), glycidyl group-containing polymers (a homopolymer of glycidyl (meth)acrylate, or a copolymer of glycidyl (meth)acrylate with another unsaturated monomer, and the like), and polyfunctional epoxides having a dimethylsiloxane skeleton (Journal of Polym. Sci., Part A, Polym. Chem., Vol. 28, 497 (1990); this document is incorporated herein by reference in its entirety).

As the oxetane can be used known substances, which include 3-ethyl-3-hydroxymethyloxetane, (3-ethyl-3-oxetanyl methoxy)methylbenzene, [1-(3-ethyl-3-oxetanyl methoxy)ethyl]phenyl ether, isobutoxymethyl (3-ethyl-3-oxetanylmethyl)ether, isobornyloxyethyl (3-ethyl-3-oxetanylmethyl)ether, isobornyl (3-ethyl-3-oxetanylmethyl)ether, 2-ethylhexyl (3-ethyl-3-oxetanylmethyl)ether, ethyldiethylene glycol (3-ethyl-3-oxetanylmethyl)ether, dicyclopentenyl oxyethyl (3-ethyl-3-oxetanylmethyl)ether, dicyclopentenyl (3-ethyl-3-oxetanylmethyl)ether, tetrahydrofurfuryl (3-ethyl-3-oxetanylmethyl)ether, tetrabromophenyl (3-ethyl-3-oxetanylmethyl)ether, 2-tetrabromophenoxyethyl (3-ethyl-3-oxetanylmethyl)ether, tribromophenyl (3-ethyl-3-oxetanylmethyl)ether, 2-tribromophenoxyethyl (3-ethyl-3-oxetanylmethyl)ether, 2-hydroxyethyl (3-ethyl-3-oxetanylmethyl)ether, 2-hydroxypropyl (3-ethyl-3-oxetanylmethyl)ether, butoxyethyl (3-ethyl-3-oxetanylmethyl)ether, pentachlorophenyl (3-ethyl-3-oxetanylmethyl)ether, pentabromophenyl (3-ethyl-3-oxetanylmethyl)ether, bornyl (3-ethyl-3-oxetanylmethyl)ether, 3,7-bis(3-oxetanyl)-5-oxanonane, 3,3'-[1,3-(2-methylenyl)propanediylbis(oxymethylene)]bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl)ether, dicyclopentenyl bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyl dimethylene (3-ethyl-3-oxetanylmethyl)ether, trimethylolpropanetris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis(3-ethyl-3-oxetanylmethyl)ether, dipentaerythritol pentakis(3-ethyl-3-oxetanylmethyl)ether, dipentaerythritol tetrakis (3-ethyl-3-oxetanylmethyl)ether, 3-ethyl-3-phenoxymethyloxetane, 3-ethyl-3-(4-methylphenoxy)methyloxetane, 3-ethyl-3-(4-fluorophenoxy)methyloxetane, 3-ethyl-3-(1-naphthoxy)methyloxetane, 3-ethyl-3-(2-naphthoxy)methyloxetane, 3-ethyl-3-{[3-(ethoxysilyl)propoxy]methyl}oxetane, oxetanylsilsesquioxetane, phenol novolak oxetane, and the like.

As the ethylenically unsaturated compound can be used known cationically polymerizable monomers, which include aliphatic monovinyl ethers, aromatic monovinyl ethers, polyfunctional vinyl ethers, styrenes, and cationically polymerizable nitrogen-containing monomers.

Examples of the aliphatic monovinyl ethers include methyl vinyl ether, ethyl vinyl ether, butyl vinyl ether, isobutyl vinyl ether, cyclohexyl vinyl ether, 2-chloroethyl vinyl ether, 2-hydroxyethyl vinyl ether, 4-hydroxybutyl vinyl ether, stearyl vinyl ether, 2-acetoxyethyl vinyl ether, diethylene glycol monovinyl ether, 2-ethylhexyl vinyl ether, dodecyl vinyl ether, octadecyl vinyl ether, allyl vinyl ether, 2-methacryloyloxyethyl vinyl ether, and 2-acryloyloxyethyl vinyl ether.

Examples of the aromatic monovinyl ethers include 2-phenoxyethyl vinyl ether, phenyl vinyl ether, and p-methoxyphenyl vinyl ether.

Examples of the polyfunctional vinyl ether include butanediol 1,4-divinyl ether, triethylene glycol divinyl ether, 1,4-benzenedivinyl ether, hydroquinone divinyl ether, cyclohexanedimethanol divinyl ether (1,4-bis[(vinyloxy)methyl]cyclohexane), diethylene glycol divinyl ether, dipropylene glycol divinyl ether, and hexanediol divinyl ether.

Examples of the styrenes include styrene, α-methylstyrene, p-methoxystyrene, and p-tert-butoxystyrene.

Examples of the cationically polymerizable nitrogen-containing monomers include N-vinylcarbazole and N-vinylpyrolidone.

Examples of the bicycloorthoester include 1-phenyl-4-ethyl-2,6,7-trioxabicyclo[2.2.2]octane and 1-ethyl-4-hydroxymethyl-2,6,7-trioxabicyclo[2.2.2]octane.

Examples of the spiroorthocarbonate include 1,5,7,11-tetraoxaspiro[5.5]undecane and 3,9-dibenzyl-1,5,7,11-tetraoxaspiro[5.5]undecane.

Examples of the spiroorthoester include 1,4,6-trioxaspiro[4.4]nonane, 2-methyl-1,4,6-trioxaspiro[4.4]nonane, and 1,4,6-trioxaspiro[4.5]decane.

Among these cationically polymerizable compounds, epoxides, oxetanes, and vinyl ethers are preferred, epoxides and oxetane are more preferred, and alicyclic epoxides and oxetanes are particularly preferred. These cationically polymerizable compounds may be used alone or two or more compounds may be used together.

The content of the photoacid generator of the present invention in an energy ray-curable composition is preferably 0.05 to 20 parts by weight, more preferably 0.1 to 10 parts by weight, based on 100 parts by weight of the cationically polymerizable compound. When being within this range, the polymerization of the cationically polymerizable compound becomes further sufficient, so that the physical properties of a cured body become still better. The content is determined by taking into consideration various factors including the properties of the cationically polymerizable compound, the kind and the amount of exposure of the energy ray, the temperature, the curing time, the humidity, and the thickness of a coating film and is not limited to the above-mentioned range.

The energy ray-curable composition of the present invention is, as necessary, allowed to contain known additives (sensitizers, pigments, fillers, antistatic agents, flame retardants, defoaming agents, flow regulators, light stabilizers, antioxidants, tackifiers, ion scavengers, solvents, nonreactive resins, radically-polymerizable compounds, and the like).

The energy ray-curable composition of the present invention, which basically needs no sensitizer, may, as necessary, contain a sensitizer as an ingredient that complements the curability. As such a sensitizer can be used known sensitizers (JP 11-279212 A, JP 09-183960 A, and the like), which include anthracenes {anthracene, 9,10-dibutoxyanthracene, 9,10-dimethoxyanthracene, 2-ethyl-9,10-dimethoxyanthracene, 2-tert-butyl-9,10-dimethoxyanthracene, 2,3-dimethyl-9,10-dimethoxyanthracene, 9-methoxy-10-methylanthracene, 9,10-diethoxyanthracene, 2-ethyl-9,10-diethoxyanthracene, 2-tert-butyl-9,10-diethoxyanthracene, 2,3-dimethyl-9,10-diethoxyanthracene, 9-ethoxy-10-methylanthracene, 9,10-dipropoxyanthracene, 2-ethyl-9,10-dipropoxyanthracene, 2-tert-butyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-tert-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-tert-9,10-di-α-methylbenzyloxyanthracene, 2,3-dimethyl-9,10-di-α-methylbenzyloxyanthracene, 9-(α-methylbenzyloxy)-10-methylanthracene, 9,10-diphenylanthracene, 9-methoxyanthracene, 9-ethoxyanthracene, 9-methylanthracene, 9-bromoanthracene, 9-methylthioanthracene, 9-ethylthioanthracene, and the like}; pyrene; 1,2-benzanthracene; perylene; tetracene; coronene; thioxanthones {thioxanthone, 2-methylthioxanthone, 2-ethylthioxanthone, 2-chlorothioxanthone, 2-isopropylthioxanthone, 2,4-diethylthioxanthone, and the like}; phenothiazine; xanthone; naphthalenes {1-naphthol, 2-naphthol, 1-methoxynaphthalene, 2-methoxynaphthalene, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bis-(2-naphthol), 4-methoxy-1-naphthol, and the like}; ketones {dimethoxyacetophenone, diethoxyacetophenone, 2-hydroxy-2-methyl-1-phenylpropan-1-one, 4'-isopropyl-2-hydroxy-2-methylpropiophenone, 2-hydroxymethyl-2-methylpropiophenone, 2,2-dimethoxy-1,2-diphenylethan-1-one, p-dimethylaminoacetophenone, p-tert-butyldichloroacetophenone, p-tert-butyltrichloroacetophenone, p-azidobenzalacetophenone, 1-hydroxycyclohexyl phenyl ketone, benzoin, benzoin methyl ether, benzoin ethyl ether, benzoin isopropyl ether, benzoin n-dibutyl ether, benzoin isobutyl ether, 1-[4-(2-hydroxyethoxy)phenyl]-2-hydroxy-2-methyl-1-propan-1-one, benzophenone, methyl o-benzoylbenzoate, Michler's ketone, 4,4'-bisdiethylaminobenzophenone, 4,4'-dichlorobenzophenone, 4-benzoyl-4'-methyldiphenylsulfide, and the like}; carbazoles {N-phenylcarbazole, N-ethylcarbazole, poly-N-vinylcarbazole, N-glycidylcarbazole, and the like}; chrysenes {1,4-dimethoxychrysene, 1,4-diethoxychrysene, 1,4-dipropoxychrysene, 1,4-dibenzyloxychrysene, 1,4-di-α-methylbenzyloxychrysene, and the like}; and phenanthrenes {9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene, 9-hydroxy-10-ethoxyphenanthrene, and the like}.

When the energy ray-curable composition of the present invention contains a sensitizer, the content of the sensitizer is preferably 1 to 300 parts by weight, more preferably 5 to 200 parts by weight, relative to 100 parts of the photoacid generator.

As a pigment can be used known pigments, which include inorganic pigments (titanium oxide, iron oxide, carbon black, and the like) and organic pigments (azo pigments, cyanine pigments, phthalocyanine pigments, quinacridone pigments, and the like).

When the energy ray-curable composition of the present invention contains a pigment, the content of the pigment is preferably 0.5 to 400000 parts by weight, more preferably 10 to 150000 parts by weight, relative to 100 parts of the photoacid generator.

As a filler can be used known fillers, which include fused silica, crystalline silica, calcium carbonate, aluminum oxide, aluminum hydroxide, zirconium oxide, magnesium carbonate, mica, talc, calcium silicate, and lithium aluminum silicate.

When the energy ray-curable composition of the present invention contains a filler, the content of the filler is preferably 50 to 600000 parts by weight, more preferably 300 to 200000 parts by weight, relative to 100 parts of the photoacid generator.

As an antistatic agent can be used known antistatic agents, which include nonionic antistatic agents {glycerol fatty acid esters, polyoxyethylene alkyl ethers, polyoxyethylene alkylphenyl ethers, N,N-bis(2-hydroxyethyl)alkylamines, polyoxyethylene alkylamines, polyoxyethylene alkylamine fatty acid esters, alkyl diethanolamides, and the like}; anionic antistatic agents {alkylsulfonic acid salts, alkylbenzene sulfonic acid salts, alkylphosphoric acid salt, and the like}; cationic antistatic agents {tetraalkylammonium salts, trialkylbenzylammonium salts, and the like}; ampholytic antistatic agents {alkylbetaine, alkylimidazolium betaine, and the like}; macromolecular antistatic agents {quaternary ammonio-containing styrene-(meth)acrylate copolymers, quaternary ammonio-containing styrene-acrylonitrile maleimide copolymers, polyoxyethylene glycol, polyetheresteramide, polyetheramidoimide, ethylene oxide-epichlorohydrin copolymers, methoxy polyoxyethylene glycol (meth)acrylate copolymers, and the like}.

When the energy ray-curable composition of the present invention contains an antistatic agent, the content of the antistatic agent is preferably 0.1 to 20000 parts by weight, more preferably 0.6 to 5000 parts by weight, relative to 100 parts of the photoacid generator.

As a flame retardant can be used known flame retardants, which include inorganic flame retardants {antimony trioxide, antimony pentoxide, tin oxide, tin hydroxide, molybdenum oxide, zinc borate, barium metaborate, red phosphorus, aluminum hydroxide, magnesium hydroxide, calcium aluminate, and the like}; bromine flame retardants {tetrabromophthalic anhydride, hexabromobenzene, decabromobiphenylether, and the like}; and phosphate flame retardants {tris(tribromophenyl) phosphate, and the like}.

When the energy ray-curable composition of the present invention contains a flame retardant, the content of the flame retardant is preferably 0.5 to 40000 parts by weight, more preferably 5 to 10000 parts by weight, relative to 100 parts of the photoacid generator.

As a defoaming agent can be used known defoaming agents, which include alcoholic defoaming agents {isopropanol, n-butanol, octaethyl alcohol, hexadecyl alcohol, and the like}; metallic soap defoaming agents {calcium stearate, aluminum stearate, and the like}; phosphate defoaming agents {tributyl phosphate, and the like}; fatty acid ester defoaming agents {glycerol monolaurate, and the like}; polyether defoaming agents {polyalkylene glycol, and the like}; silicone defoaming agents {dimethyl silicone oil, silica-silicone compound, and the like}; and mineral oil defoaming agents {mineral oil in which a silica powder is dispersed, and the like}.

When the energy ray-curable composition of the present invention contains a defoaming agent, the content of the defoaming agent is preferably 0.1 to 20000 parts by weight, more preferably 0.5 to 5000 parts by weight, relative to 100 parts of the photoacid generator.

As a flow regulator can be used known flow regulators, which include hydrogenated castor oil, oxidized polyethylene, organic bentonite, colloidal silica, amide wax, metallic soap, and acrylic ester polymers.

When the energy ray-curable composition of the present invention contains a flow regulator, the content of the flow regulator is preferably 0.1 to 20000 parts by weight, more preferably 0.5 to 5000 parts by weight, relative to 100 parts of the photoacid generator.

As a light stabilizer can be used known light stabilizers, which include ultraviolet absorbing type stabilizers {benzotriazol, benzophenone, salicylates, cyanoacrylates, their derivatives, and the like}; radical scavenging type stabilizers {hindered amines, and the like}; and quenching type stabilizers {nickel complexes, and the like}.

When the energy ray-curable composition of the present invention contains a light stabilizer, the content of the light stabilizer is preferably 0.05 to 40000 parts by weight, more preferably 0.5 to 10000 parts by weight, relative to 100 parts of the photoacid generator.

As an antioxidant can be used known antioxidants, which include phenolic antioxidants (monophenolic, bisphenolic, macromolecular phenolic, and the like), sulfur-containing antioxidants, and phosphorus-containing antioxidants.

When the energy ray-curable composition of the present invention contains an antioxidant, the content of the antioxidant is preferably 0.1 to 20000 parts by weight, more preferably 0.6 to 5000 parts by weight, relative to 100 parts of the photoacid generator.

As a tackifier can be used known antioxidants, which include coupling agents, silane coupling agents and titanium coupling agents.

When the energy ray-curable composition of the present invention contains a tackifier, the content of the tackifier is preferably 0.1 to 20000 parts by weight, more preferably 0.6 to 5000 parts by weight, relative to 100 parts of the tackifier.

As an ion scavenger can be used known ion scavengers, which include organic aluminum (alkoxyaluminum, phenoxyaluminum, and the like).

When the energy ray-curable composition of the present invention contains an ion scavenger, the content of the ion scavenger is preferably 0.1 to 20000 parts by weight, more preferably 0.6 to 5000 parts by weight, relative to 100 parts of the photoacid generator.

A solvent, which is not restricted as far as it can be used for dissolving a cationically polymerizable compound or adjusting the viscosity of an energy ray-curable composition, includes ethers {anisole, diethyl ether, tetrahydrofuran, 1,4-dioxane, ethyl-tert-butyl ether, and the like}; aromatic hydrocarbons {toluene, xylene, cumene, ethylbenzene, mesitylene, and the like}; ketones {acetone, methyl ethyl ketone, isobutyl ketone, cyclohexanone, and the like}; alcohols {methanol, ethanol, isopropyl alcohol, tert-butanol, and the like}; and nitriles {acetonitrile, and the like}.

When the energy ray-curable composition of the present invention contains a solvent, the content of the solvent is preferably 50 to 2000000 parts by weight, more preferably 200 to 500000 parts by weight, relative to 100 parts of the photoacid generator.

Examples of a nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of these resins is preferably 1000 to 500000, more preferably 5000 to 100000 (the number average molecular weight is a value measured by a general method, such as GPC).

When the energy ray-curable composition of the present invention contains a nonreactive resin, the content of the nonreactive resin is preferably 5 to 400000 parts by weight, more preferably 50 to 150000 parts by weight, relative to 100 parts of the photoacid generator.

When making a nonreactive resin be contained, it is desirable to dissolve the resin in a solvent in advance in order to make the nonreactive resin easy to dissolve in a cationically polymerizable compound and the like.

As a radically-polymerizable compound can be used known {"Photopolymer Handbook" edited by The Technical Association of Photopolymers, Japan (1989, Kogyo Chosakai Publishing, Inc.), "Technology of UV/EB Curing", edited by Sogo Gijutsu Center (1982, Sogo Gijutsu Center), "UV/EB Curable Materials", edited by RadTech (1992, CMC), and "Causes of UV Curing Defects/Inhibition and Remedies Therefor", edited by Technical Information Institute (2003, Technical Information Institute)} radically-polymerizable compounds, which include monofunctional monomers, bifunctional monomers, polyfunctional monomers, epoxy (meth)acrylate, polyester (meth)acrylate, and urethane (meth)acrylate.

Examples of the monofunctional monomers include methyl (meth)acrylate, ethyl (meth)acrylate, 2-ethylhexyl (meth)acrylate, lauryl (meth)acrylate, 2-hydroxyethyl (meth)acrylate, 1,6-hexanediol mono(meth)acrylate, styrene, vinylcyclohexene, isobutylene, and butadiene.

Examples of the bifunctional monomers include di(meth)acrylates of dihydric alcohols or their alkylene oxide adducts {di(meth)acrylates of dihydric alcohols (ethylene glycol, propylene glycol, bisphenol A, hydrogenated bisphenol A, their alkylene oxide adducts, and the like)}, and divinylbenzene.

As the polyfunctional monomers can be used monomers other than bifunctional monomers, which include (meth)acrylates of polyhydric alcohols (trimethylolpropane, glycerol, pentaerythritol, their alkylene oxide adducts, and the like).

Examples of the epoxy (meth)acrylate include epoxy (meth)acrylates which are produced by making an epoxide (an aromatic epoxide, an alicyclic epoxide, an aliphatic epoxide, or the like} and (meth)acrylic acid react together.

Examples of the polyester (meth)acrylate include polyester (meth)acrylates obtained by esterifying, with (meth)acrylic acid, a hydroxy-terminated polyester obtained from an aromatic polybasic acid (phthalic acid, isophthalic acid, terephthalic acid, trimellitic acid, pyromellitic acid, or the like) or an aliphatic polybasic acid (succinic acid, adipic acid, sebacic acid, or the like) and a polyhydric alcohol (ethylene glycol, diethylene glycol, polyethylene glycol, propylene glycol, dipropylene glycol, polypropylene glycol, neopentyl glycol, polytetramethylene glycol, 1,3-butanediol, 1,4-butanediol, 1,6-hexanediol, trimethylolpropane, glycerol, pentaerythritol, bisphenol, their alkylene oxide adducts, or the like).

Examples of the urethane (meth)acrylate include urethane (meth)acrylate resulting from a urethanization reaction between an isocyanate-terminated prepolymer obtained from a polyfunctional isocyanate {alicyclic isocyanates (isophorone diisocyanate, dicyclohexylmethane diisocyanate, and the like), aliphatic isocyanates (tetramethylene diisocyanate, hexamethylene diisocyanate, and the like), aromatic isocyanates (toluene diisocyanate, phenylene diisocyanate, diphenylmethane diisocyanate, and the like), and the like} and a polyhydric alcohol {ethylene glycol, diethylene glycol, polyethylene glycol, propylene glycol, polypropylene glycol, neopentyl glycol, polytetramethylene glycol, 1,3-butanediol, 1,4-butanediol, 1,6-hexanediol, trimethylolpropane, glycerol, pentaerythritol, bisphenol, hydrogenated bisphenol, polycaprolactone diol, polyesterdiol, polycarbonatediol, and the like} and a hydroxy group-containing (meth)acrylate {2-hydroxylethyl (meth)acrylate, 2-hydroxypropyl (meth)acrylate, 4-hydroxybutyl (meth)acrylate, tri(meth)acrylate of pentaerythritol, and the like}.

When the energy ray-curable composition of the present invention contains a radically-polymerizable compound, the content of the radically-polymerizable compound is preferably 5 to 400000 parts by weight, more preferably 50 to 150000 parts by weight, relative to 100 parts of the photoacid generator.

When the energy ray-curable composition of the present invention contains a radically-polymerizable compound, it is preferable to use a radical polymerization initiator which starts polymerization by heat or light in order to polymerize the radically-polymerizable compound by radical polymerization.

As the radical polymerization initiator can be used known radical polymerization initiators, which include heat radical polymerization initiators and a photoradical polymerization initiators.

Examples of the heat radical polymerization initiator include organic peroxides {ketone peroxides (methyl ethyl ketone peroxide, cyclohexanone peroxide, and the like), peroxyketals (2,2-bis(tert-butylperoxy)butane, 1,1-bis(tert-butylperoxy)cyclohexane, and the like), hydroperoxides (tert-butyl hydroperoxide, cumene hydroperoxide, and the like), dialkyl peroxides (di-tert-butyl peroxide, and the like), diacyl peroxides (isobutyryl peroxide, lauroyl peroxide, benzoyl peroxide, and the like), peroxydicarbonates (diisopropyl peroxydicarbonate, and the like), peroxyesters (tert-butylperoxyisobutyrate, 2,5-dimethyl-2,5-di(benzoylperoxy)hexane, and the like), and the like}, and azo compounds {1,1'-azobis(cyclohexane-1-carbonitrile), 2,2'-azobisisobutyronitrile, 2,2'-azobis(2,4-dimethyl-4-methoxyvaleronitrile), 2,2'-azobis(2-methylpropionamidin) dihydrochloride, 2,2'-azobis[2-methyl-N-(2-propenyl)propionamidine]dihydrochloride, 2,2'-azobis(2-methylpropionamide), 2,2'-azobis[2-methyl-N-(2-hydroxyethyl)propionamide], 2,2'-azobis(2-methylpropane), 2,2'-azobis(2,4,4-trimethylpentane), dimethyl 2,2'-azobis(2-methyl propionate), and the like}.

Examples of the photoradical polymerization initiator include acetophenone initiators {acetophenone, p-tert-butyltrichloroacetophenone, 2,2-diethoxyacetophenone, and the like}, benzophenone initiators {benzophenone, methyl o-benzoylbenzoate, 4-benzoyl-4'-methyldiphenylsulfide, and the like}, Michler's ketone initiators {4,4'-bis(dimethylamino)benzophenone, 4,4'-bis(diethylamino)benzophenone, and the like}, benzoin initiators {benzoin, benzoin methyl ether, and the like}, thioxanthone initiators {thioxanthone, 2-methylthioxanthone, 2-ethylthioxanthone, 2-chlorothioxanthone, 2-isopropylthioxanthone, 2,4-diethylthioxanthone, and the like}, and acylphosphine initiators {monoacylphosphine oxide, bisacylphosphine oxide, and the like}.

When the energy ray-curable composition of the present invention contains a radical polymerization initiator, the content of the radical polymerization initiator is preferably 0.01 to 20 parts by weight, more preferably 0.1 to 10 parts by weight, relative to 100 parts of the radically-polymerizable compound.

The energy ray-curable composition of the present invention can be prepared by uniformly mixing and dissolving a cationically polymerizable compound, a photoacid generator and, as necessary, an additive at room temperature (about 20 to 30° C.) or, as necessary, under heating (about 40 to 90° C.), or further kneading them with a triple-roller kneader, or the like.

The energy ray-curable composition of the present invention can be cured to afford a cured body by being irradiated with energy rays.

The energy rays, which may be any rays as far as they have energy strong enough to induce decomposition of the sulfonium salt of the present invention, are preferably energy rays in the ultraviolet to visible region (wavelength: from about 100 to about 800 nm) obtained from a low pressure-, medium pressure-, high pressure-, or ultra-high pressure-mercury lamp, a metal halide lamp, an LED lamp, a xenon lamp, a carbon arc lamp, a fluorescent lamp, semiconductor solid state laser, argon laser, He—Cd laser, KrF excimer laser, ArF excimer laser, $F_2$ laser, or the like. Radiation with a high energy, such as electron beams or X-rays, can also be used as the energy rays.

Although the irradiation time of the energy rays is influenced by the intensity of the energy rays and the permeability of an energy ray-curable composition to the energy rays, about 0.1 to 10 seconds is sufficient at normal temperature (about 20 to 30° C.). However, if the permeability to energy rays is low or if the thickness of an energy ray-curable composition is large, for example, it is sometimes preferred to spend more time. Although most energy ray-curable compositions are cured by cationic polymerization in 0.1 seconds to several minutes after the energy ray irradiation, post-curing may be performed as necessary by heating for several seconds to several hours at room temperature (about 20 to 30° C.) to 150° C. after the irradiation of the energy rays.

Among energy ray-curable compositions of the present invention, one which contains a sulfonium salt in which $R^2$ and/or $R^3$ is an alkyl group can be cured also by heating. The heating temperature is preferably approximately from 50 to 250° C., more preferably from 80 to 200° C. The heating time is from several minutes to several hours.

Specific applications of the energy ray-curable composition of the present invention include paint, a coating agent, ink, resist (positive resist, chemically amplified resist, and negative resist), a resist film, a photosensitive material, an adhesive, a molding material, a casting material, putty, a glass fiber impregnant, a filler, a sealing material, a sealant, a material of stereolithography, and so on.

Since the sulfonium salt of the present invention generates a strong acid through exposure to light, it can be used, for example, as a photoacid generator for known chemical amplification type resist materials (JP 2003-267968 A, JP 2003-261529 A (corresponding U.S. Pat. Appl. Nos. 2003/0207201 and 2003/0235779), JP 2002-193925 A (corresponding U.S. Pat. No. 6,723,483), and the like; these documents are incorporated herein by reference in their entirety).

The chemical amplification type resist materials include (1) a two-component chemical amplification type positive resist containing, as essential ingredients, a photoacid generator and a resin that becomes soluble in an alkali developing solution by the action of an acid, (2) a three-component chemical amplification type positive resist containing, as essential ingredients, a resin that is soluble in an alkali developing solution, a dissolution inhibitor that becomes soluble in an alkali developing solution by the action of an acid, and a photoacid generator, and (3) a chemical amplification type negative resist containing, as essential ingredients, a resin that is soluble in an alkali developing solution, a crosslinking agent that crosslinks a resin through heating treatment in the presence of an acid to make the resin insoluble in an alkali developing solution, and a photoacid generator.

EXAMPLES

The following examples further illustrate the present invention, but the invention is not limited thereto. Unless otherwise stated, part(s) and % mean part(s) by weight and % by weight, respectively.

Production Example 1

Synthesis of 2-(phenylthio)thioxanthone

After mixing 11.0 parts of 2-chlorothioxanthone, 4.9 parts of thiophenol, 2.5 parts of potassium hydroxide, and 162 parts of N,N-dimethylformamide uniformly and then making them react at 130° C. for 9 hours, the reaction solution was cooled to room temperature (about 25° C.) and then was poured into 200 parts of distilled water, so that the product was precipitated. This was filtered and the residue was washed with water until the pH of the filtrate became neutral. Then the residue was dried under reduced pressure, affording a yellow powdery product. The product was purified by column chromatography (eluate:toluene/hexane=1/1:volume ratio) to afford 2-(phenylthio)thioxanthone in a yield of 45%. The product was identified by $^1$H-NMR {d6-dimethyl sulfoxide, δ (ppm) 8.43 (1H, d), 8.25 (1H, s), 7.75-7.90 (3H, m), 7.66 (1H, d), 7.60 (1H, t), 7.42-7.46 (5H, m)}.

Production Example 2

Synthesis of 2-[(phenyl)sulfinyl]thioxanthone

While 11.2 parts of 2-(phenylthio)thioxanthone synthesized in Production Example 1, 215 parts of acetonitrile, and 0.02 parts of sulfuric acid were stirred at 40° C., 4.0 parts of a 30% aqueous hydrogen peroxide solution was dropped thereto slowly and then a reaction was performed at 40 to 45° C. for 14 hours. Subsequently, the reaction solution was cooled to room temperature (about 25° C.) and then was poured into 200 parts of distilled water, so that the product was precipitated. This was filtered and the residue was washed with water until the pH of the filtrate became neutral. Then the residue was dried under reduced pressure, affording a yellow powdery product. The product was purified by column chromatography (eluate: ethyl acetate/toluene=⅓:volume ratio) to afford 2-[(phenyl)sulfinyl]thioxanthone in a yield of 83%. The product was identified by $^1$H-NMR {d6-dimethyl sulfoxide, δ (ppm) 8.75 (1H, s), 8.45 (1H, d), 8.01 (2H, d), 7.75-7.85 (4H, m), 7.53-7.62 (4H, m)}.

Example 1

Synthesis of [4-(2-thioxanthonylthio)phenyl]phenyl-2-thioxanthonylsulfonium tris(pentafluoroethyl)trifluorophosphate (10)

While 4.3 parts of 2-(phenylthio)thioxanthone synthesized in Production Example 1, 4.5 parts of 2-[(phenyl)sulfinyl]thioxanthone synthesized in Production Example 2, 4.1 parts of acetic anhydride, and 110 parts of acetonitrile were stirred at 40° C., 2.4 parts of trifluoromethanesulfonic acid was dropped thereto slowly, and a reaction was carried out at 40 to 45° C. for 1 hour. Then, the reaction solution was cooled to room temperature (about 25° C.), poured into 150 parts of distilled water, extracted with chloroform, and washed with water until the pH of the aqueous phase became neutral. After the chloroform phase was transferred to a rotary evaporator and the solvent was evaporated, the formed solid was washed by repeating three times an operation involving addition of 50 parts of toluene, dispersion in toluene using an ultrasonic washer, standing for about 15 minutes, and subsequent removal of a supernatant liquid. Subsequently, the solid was transferred to a rotary evaporator and the solvent was distilled off, so that [4-(2-thioxanthonylthio)phenyl]phenyl-2-thioxanthonylsulfonium triflate (triflate=trifluoromethanesulfonate anion) was obtained. This triflate was dissolved in 212 parts of dichloromethane and was poured into 65 parts of a 10% aqueous potassium tris(pentafluoroethyl)trifluorophosphate solution, followed by stirring at room temperature (about 25° C.) for 2 hours. After the dichloromethane layer was washed with water three times by a separatory operation, it was transferred to a rotary evaporator and the solvent was distilled off, so that [4-(2-thioxanthonylthio)phenyl]phenyl-2-thioxanthonylsulfonium tris(pentafluoroethyl)trifluorophosphate was obtained in a yield of 95%. The product was identified by $^1$H-NMR {d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)}. Absorption caused by a P—F binding was confirmed near 840 cm$^{-1}$ by infrared spectrophotometric analysis (the KBr tablet method).

[Chem. 15]

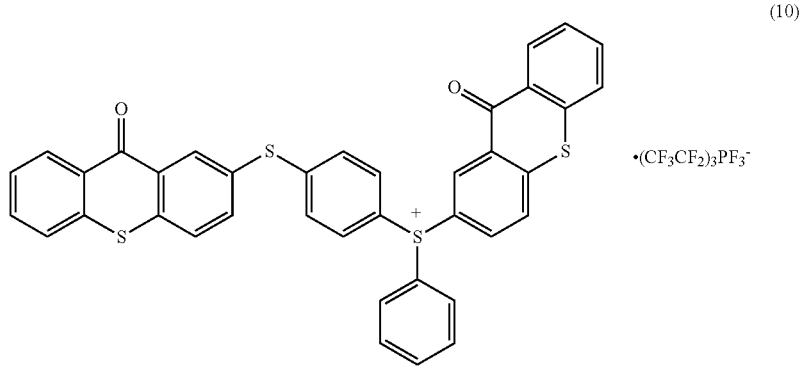

(10)

Example 2

Synthesis of a mixture containing [4-(2-thioxanthonylthio)phenyl]phenyl-2-thioxanthonylsulfonium tris(pentafluoroethyl)trifluorophosphate (10) and [4-(2-thioxanthonylthio)phenyl]diphenylsulfonium tris(pentafluoroethyl)trifluorophosphate (20)

While 10.0 parts of 2-(phenylthio)thioxanthone synthesized in Production Example 1, 6.3 parts of diphenyl sulfoxide, 9.6 parts of acetic anhydride, and 273 parts of acetonitrile were stirred at 40° C., 5.7 parts of trifluoromethanesulfonic acid was dropped thereto slowly and then a reaction was performed at 40 to 45° C. for 3 hours. Subsequently, the reaction solution was cooled to room temperature (about 25° C.) and then was poured into 300 parts of distilled water, so that the product was precipitated. This was filtered and the residue was washed with water until the pH of the filtrate became neutral and then the residue was dried under reduced pressure. Subsequently, the formed solid was washed by repeating three times an operation involving addition of 100 parts of diethyl ether, dispersion in diethyl ether using an ultrasonic washer, standing for about 15 minutes, and subsequent removal of a supernatant liquid, and the solvent was distilled off by a rotary evaporator, so that a yellow powdery solid was obtained. The yellow powdery solid was dissolved in 200 parts of dichloromethane and was poured into 103 parts of a 10% aqueous potassium tris(pentafluoroethyl)trifluorophosphate solution, followed by stirring at room temperature (about 25° C.) for 2 hours. The organic layer was washed with water several times and was dried under reduced pressure, affording a mixture containing 11% of [4-(2-thioxanthonylthio)phenyl]phenyl-2-thioxanthonylsulfonium tris(pentafluoroethyl)trifluorophosphate and 18% of [4-(2-thioxanthonylthio)phenyl]diphenylsulfonium tris(pentafluoroethyl)trifluorophosphate {in addition, containing 19% of 4-(phenylthio)phenyldiphenylsulfonium tris(pentafluoroethyl)trifluorophosphate and 52% of phenyl-4-(phenylthio)phenylthioxanthonylsulfonium tris(pentafluoroethyl)trifluorophosphate}. From this mixture were separated fractions under the following HPLC fractioning conditions, and the fractions were identified by $^1$H-NMR. The content of each fraction was quantified by producing a calibration curve under the following HPLC conditions. For each fraction, absorption caused by a P—F binding was confirmed near 840 cm$^{-1}$ by infrared spectrophotometric analysis (the KBr tablet method).

(HPLC Fractioning Conditions)
Instrument: Waters 600 controller (manufactured by Nihon Waters KK.)
Column: Shodex K-2001 (manufactured by Showa Denko K.K.)
Eluate: chloroform
Flow rate: 3 ml/min.
Column temperature: 40° C.
Detector: Waters2414 differential refractometer (manufactured by Nihon Waters K.K.)
Fractionation interval: 30 seconds
Injection amount: 500 μL NMR, Data

[4-(2-Thioxanthonylthio)phenyl]phenyl-2-thioxanthonylsulfonium tris(pentafluoroethyl)trifluorophosphate d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)

[4-(2-Thioxanthonylthio)phenyl]diphenylsulfonium tris(pentafluoroethyl)trifluorophosphate d6-dimethyl sulfoxide, δ (ppm) 8.53 (1H, s), 8.47 (1H, s), 8.00 (1H, d), 7.69-7.92 (15H, m), 7.65 (1H, t), 7.54 (2H, d)

4-(Phenylthio)phenyldiphenylsulfonium tris(pentafluoroethyl)trifluorophosphate d6-dimethyl sulfoxide, δ (ppm) 7.72-7.87 (12H, m), 7.54-7.63 (5H, m), 7.42 (2H, d)

Phenyl-4-(phenylthio)phenylthioxanthonylsulfonium tris(pentafluoroethyl)trifluorophosphate d6-dimethyl sulfoxide, δ (ppm) 8.70 (1H, s), 8.46 (1H, d), 8.26 (1H, d), 8.07 (1H, d), 7.53-7.98 (10H, m), 7.42-7.46 (3H, m)

(HPLC Conditions)
Instrument: LaChrom D-7000 (manufactured by Hitachi, Ltd.)
Column: Inertsil Ph-3 (4.6 mmi. d.×250 mm, manufactured by GL Sciences Inc.)
Eluate methanol/water/sodium perchlorate=87/10/3 (weight ratio)

Flow rate: 1 ml/min.

Column temperature: 40° C.

Detector: L-7455 type diode array detector (manufactured by Hitachi, Ltd.)

Example 3

Synthesis of [4-(2-thioxanthonylthio)phenyl]diphenylsulfonium tris(pentafluoroethyl)trifluorophosphate (30)

While 10.0 parts of dithiosalicylic acid and 300 parts of sulfuric acid were stirred, 16.8 parts of 4-(phenylthio)phenyl-diphenyl sulfonium pentafluoro phosphate was added thereto slowly, and then a reaction was performed at room temperature (about 25° C.) for 1 hour. Subsequently, the reaction solution was poured into 3000 parts of distilled water, so that the product was precipitated. This was filtered and the residue was washed with water until the pH of the filtrate became neutral, so that a solid was obtained. This solid was dissolved in 390 parts of methanol and was poured into 997 parts of a 10% aqueous potassium tris(pentafluoroethyl)trifluorophosphate solution, followed by stirring at room temperature (about 25° C.) for 2 hours. The organic layer was washed with water several times and was dried under reduced pressure, affording [4-(2-thioxanthonylthio)phenyl]diphenylsulfonium tris(pentafluoroethyl)trifluorophosphate in a yield of 80%. The product was identified by $^1$H-NMR, {d6-dimethyl sulfoxide, δ (ppm) 8.53 (1H, s), 8.47 (1H, d), 8.00 (1H, d), 7.69-7.92 (15H, m), 7.65 (1H, t), 7.54 (2H, d)}. Absorption caused by a P—F binding was confirmed near 840 cm$^{-1}$ by infrared spectrophotometric analysis (the KBr tablet method).

[Chem. 16]

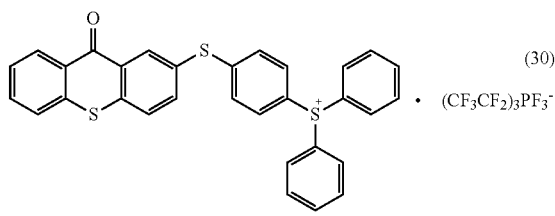

(30)

· (CF$_3$CF$_2$)$_3$PF$_3^-$

Example 4

Synthesis of [4-(2-thioxanthonylthio)phenyl]phenyl-2-thioxanthonylsulfonium hexafluoroantimonate (40)

[4-(2-Thioxanthonylthio)phenyl]phenyl-2-thioxanthonylsulfonium hexafluoroantimonate (40) was obtained in a yield of 95% in the same manner as in Example 1, except for changing "65 parts of a 10% aqueous potassium tris(pentafluoroethyl)trifluorophosphate solution" to "73.8 parts of 5% potassium hexafluoroantimonate." The product was identified by $^1$H-NMR {d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)}. Absorption caused by a Sb—F binding was confirmed near 650 cm$^{-1}$ by infrared spectrophotometric analysis (the KBr tablet method).

Example 5

Synthesis of a mixture containing [4-(2-thioxanthonylthio)phenyl]phenyl-2-thioxanthonylsulfonium hexafluoroantimonate (40) and [4-(2-thioxanthonylthio)phenyl]diphenylsulfonium hexafluoroantimonate (50)

A mixture containing 11% of [4-(2-thioxanthonylthio)phenyl]phenyl-2-thioxanthonylsulfonium hexafluoroantimonate and 18% of [4-(2-thioxanthonylthio)phenyl]diphenylsulfonium hexafluoroantimonate {in addition, containing 19% of 4-(phenylthio)phenyldiphenylsulfonium hexafluoroantimonate and 52% of phenyl-4-(phenylthio)phenylthioxanthonylsulfonium hexafluoroantimonate} was obtained in the same manner as in Example 2, except for changing "103 parts of a 10% aqueous potassium tris(pentafluoroethyl)trifluorophosphate solution" to "117.0 parts of 5% potassium hexafluoroantimonate." From this mixture were separated fractions under HPLC fractioning conditions which were the same as in Example 2, and the fractions were identified by $^1$H-NMR. The content of each fraction was quantified by producing a calibration curve under HPLC conditions which were the same as in Example 2. For each fraction, absorption caused by a Sb—F binding was confirmed near 650 cm$^{-1}$ by infrared spectrophotometric analysis (the KBr tablet method).

NMR, Data

[4-(2-Thioxanthonylthio)phenyl]phenyl-2-thioxanthonylsulfonium hexafluoroantimonate d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)

[4-(2-Thioxanthonylthio)phenyl]diphenylsulfonium hexafluoroantimonate d6-dimethyl sulfoxide, δ (ppm) 8.53 (1H, s), 8.47 (1H, s), 8.00 (1H, d), 7.69-7.92 (15H, m), 7.65 (1H, t), 7.54 (2H, d)

4-(Phenylthio)phenyldiphenylsulfonium hexafluoroantimonate d6-dimethyl sulfoxide, δ (ppm) 7.72-7.87 (12H, m), 7.54-7.63 (5H, m), 7.42 (2H, d)

Phenyl-4-(phenylthio)phenylthioxanthonylsulfonium hexafluoroantimonate d6-dimethyl sulfoxide, δ (ppm) 8.70 (1H, s), 8.46 (1H, d), 8.26 (1H, d), 8.07 (1H, d), 7.53-7.98 (10H, m), 7.42-7.46 (3H, m)

Example 6

Synthesis of [4-(2-thioxanthonylthio)phenyl]diphenylsulfonium hexafluoroantimonate (60)

[4-(2-Thioxanthonylthio)phenyl]diphenylsulfonium hexafluoroantimonate (60) was obtained in a yield of 78% in the same manner as in Example 3, except for changing "997 parts of a 10% aqueous potassium tris(pentafluoroethyl)trifluorophosphate solution" to "1132 parts of 5% potassium hexafluoroantimonate." The product was identified by $^1$H-NMR, {d6-dimethyl sulfoxide, δ (ppm) 8.53 (1H, s), 8.47 (1H, d), 8.00 (1H, d), 7.69-7.92 (15H, m), 7.65 (1H, t), 7.54 (2H, d)}. Absorption caused by a Sb—F binding was confirmed near 650 cm$^{-1}$ by infrared spectrophotometric analysis (the KBr tablet method).

Example 7

Synthesis of [4-(2-thioxanthonylthio)phenyl]phenyl-2-thioxanthonylsulfonium tetrakis(pentafluorophenyl)borate (70)

[4-(2-Thioxanthonylthio)phenyl]phenyl-2-thioxanthonylsulfonium tetrakis(pentafluorophenyl)borate (70) was obtained in a yield of 95% in the same manner as in Example 1, except for changing "65 parts of a 10% aqueous potassium tris(pentafluoroethyl)trifluorophosphate solution" to "92.1 parts of 10% lithium tetrakis(pentafluorophenyl)borate." The product was identified by $^1$H-NMR {d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)}. Absorption caused by a B—C binding was confirmed near 980 cm$^{-1}$ by infrared spectrophotometric analysis (the KBr tablet method).

Example 8

Synthesis of a mixture containing [4-(2-thioxanthonylthio)phenyl]phenyl-2-thioxanthonylsulfonium tetrakis(pentafluorophenyl)borate (70) and [4-(2-thioxanthonylthio)phenyl]diphenylsulfonium tetrakis (pentafluorophenyl)borate (80)

A mixture containing 11% of [4-(2-thioxanthonylthio)phenyl]phenyl-2-thioxanthonylsulfonium tetrakis(pentafluorophenyl)borate and 18% of [4-(2-thioxanthonylthio)phenyl]diphenylsulfonium tetrakis(pentafluorophenyl)borate {in addition, containing 19% of 4-(phenylthio)phenyldiphenylsulfonium tetrakis(pentafluorophenyl)borate and 52% of phenyl-4-(phenylthio)phenylthioxanthonylsulfonium tetrakis(pentafluorophenyl)borate} was obtained in the same manner as in Example 2, except for changing "103 parts of a 10% aqueous potassium tris(pentafluoroethyl)trifluorophosphate solution" to "146 parts of 10% lithium tetrakis (pentafluorophenyl)borate." From this mixture were separated fractions under HPLC fractioning conditions which were the same as in Example 2, and the fractions were identified by $^1$H-NMR. The content of each fraction was quantified by producing a calibration curve under HPLC conditions which were the same as in Example 2. For each fraction, absorption caused by a B—C binding was confirmed near 980 cm$^{-1}$ by infrared spectrophotometric analysis (the KBr tablet method).

NMR Data

[4-(2-Thioxanthonylthio)phenyl]phenyl-2-thioxanthonylsulfonium tetrakis(pentafluorophenyl)borate d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)

[4-(2-Thioxanthonylthio)phenyl]diphenylsulfonium tetrakis(pentafluorophenyl)borate d6-dimethyl sulfoxide, δ (ppm) 8.53 (1H, s), 8.47 (1H, s), 8.00 (1H, d), 7.69-7.92 (15H, m), 7.65 (1H, t), 7.54 (2H, d)

4-(Phenylthio)phenyldiphenylsulfonium tetrakis(pentafluorophenyl)borate d6-dimethyl sulfoxide, δ (ppm) 7.72-7.87 (12H, m), 7.54-7.63 (5H, m), 7.42 (2H, d)

Phenyl-4-(phenylthio)phenylthioxanthonylsulfonium tetrakis(pentafluorophenyl)borate d6-dimethyl sulfoxide, δ (ppm) 8.70 (1H, s), 8.46 (1H, d), 8.26 (1H, d), 8.07 (1H, d), 7.53-7.98 (10H, m), 7.42-7.46 (3H, m)

Example 9

Synthesis of [4-(2-thioxanthonylthio)phenyl]diphenylsulfonium tetrakis(pentafluorophenyl)borate (90)

[4-(2-Thioxanthonylthio)phenyl]diphenylsulfonium tetrakis(pentafluorophenyl)borate (90) was obtained in a yield of 79% in the same manner as in Example 3, except for changing "997 parts of a 10% aqueous potassium tris(pentafluoroethyl)trifluorophosphate solution" to "1413 parts of 10% lithium tetrakis(pentafluorophenyl)borate." The product was identified by $^1$H-NMR {d6-dimethyl sulfoxide, δ (ppm) 8.53 (1H, s), 8.47 (1H, d), 8.00 (1H, d), 7.69-7.92 (15H, m), 7.65 (1H, t), 7.54 (2H, d)}. Absorption caused by a B—C binding was confirmed near 980 cm$^{-1}$ by infrared spectrophotometric analysis (the KBr tablet method).

Example 10

Synthesis of [4-(2-thioxanthonylthio)phenyl]phenyl-2-thioxanthonylsulfonium hexafluorophosphate (110)

[4-(2-Thioxanthonylthio)phenyl]phenyl-2-thioxanthonylsulfonium hexafluorophosphate (110) was obtained in a yield of 95% in the same manner as in Example 1, except for changing "65 parts of a 10% aqueous potassium tris(pentafluoroethyl)trifluorophosphate solution" to "49.4 parts of 5% potassium hexafluorophosphate." The product was identified by $^1$H-NMR, {d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)}. Absorption caused by a P—F binding was confirmed near 840 cm$^{-1}$ by infrared spectrophotometric analysis (the KBr tablet method).

Example 11

Synthesis of a mixture containing [4-(2-thioxanthonylthio)phenyl]phenyl-2-thioxanthonylsulfonium hexafluorophosphate (110) and [4-(2-thioxanthonylthio)phenyl]diphenylsulfonium hexafluorophosphate (120)

A mixture containing 11% of [4-(2-thioxanthonylthio)phenyl]phenyl-2-thioxanthonylsulfonium hexafluorophosphate and 18% of [4-(2-thioxanthonylthio)phenyl]diphenylsulfonium hexafluorophosphate {in addition, containing 19% of 4-(phenylthio)phenyldiphenylsulfonium hexafluorophosphate and 52% of phenyl-4-(phenylthio)phenylthioxanthonylsulfonium hexafluorophosphate} was obtained in the same manner as in Example 2, except for changing "103 parts of a 10% aqueous potassium tris(pentafluoroethyl)trifluorophosphate solution" to "78.3 parts of 5% potassium hexafluorophosphate." From this mixture were separated fractions under HPLC fractioning conditions which were the same as in Example 2, and the fractions were identified by $^1$H-NMR. The content of each fraction was quantified by producing a calibration curve under HPLC conditions which were the same as in Example 2. For each fraction, absorption caused by a P—F binding was confirmed at 840 cm$^{-1}$ by infrared spectrophotometric analysis (the KBr tablet method).

NMR, Data

[4-(2-Thioxanthonylthio)phenyl]phenyl-2-thioxanthonylsulfonium hexafluorophosphate d6-dimethyl sulfoxide, δ (ppm) 8.72 (1H, s), 8.54 (1H, s), 8.46 (2H, d), 8.27 (1H, d), 7.76-8.10 (14H, m), 7.60-7.69 (4H, m)

[4-(2-Thioxanthonylthio)phenyl]diphenylsulfonium hexafluorophosphate d6-dimethyl sulfoxide, δ (ppm) 8.53 (1H, s), 8.47 (1H, s), 8.00 (1H, d), 7.69-7.92 (15H, m), 7.65 (1H, t), 7.54 (2H, d)

4-(Phenylthio)phenyldiphenylsulfonium hexafluorophosphate d6-dimethyl sulfoxide, δ (ppm) 7.72-7.87 (12H, m), 7.54-7.63 (5H, m), 7.42 (2H, d)

Phenyl-4-(phenylthio)phenylthioxanthonylsulfonium hexafluorophosphate d6-dimethyl sulfoxide, δ (ppm) 8.70 (1H, s), 8.46 (1H, d), 8.26 (1H, d), 8.07 (1H, d), 7.53-7.98 (10H, m), 7.42-7.46 (3H, m)

Example 12

Synthesis of [4-(2-thioxanthonylthio)phenyl]diphenylsulfonium hexafluorophosphate (130)

[4-(2-Thioxanthonylthio)phenyl]diphenylsulfonium hexafluorophosphate (130) was obtained in a yield of 79% in the same manner as in Example 3, except for changing "997 parts of a 10% aqueous potassium tris(pentafluoroethyl)trifluorophosphate solution" to "758 parts of 5% potassium hexafluorophosphate." The product was identified by $^1$H-NMR {d6-dimethyl sulfoxide, δ (ppm) 8.53 (1H, s), 8.47 (1H, d), 8.00 (1H, d), 7.69-7.92 (15H, m), 7.65 (1H, t), 7.54 (2H, d)}. Absorption caused by a P—F binding was confirmed near 840 cm$^{-1}$ by infrared spectrophotometric analysis (the KBr tablet method).

Comparative Example 1

Synthesis of diphenyl-2-thioxanthonylsulfonium tris(pentafluoroethyl)trifluorophosphate (H10)

After mixing 15.0 parts of 2-(phenylthio)thioxanthone produced in Production Example 1, 41.9 parts of diphenyliodonium hexafluorophosphate, 0.4 parts of copper(II) benzoate, and 300 parts of chlorobenzene uniformly and then making them react at 120 to 125° C. for 3 hours, the reaction solution was cooled to room temperature (about 25° C.) and then was poured into 300 parts of distilled water, so that the product was precipitated. This was filtered and the residue was washed with water until the pH of the filtrate became neutral and then the residue was dried under reduced pressure. Subsequently, the formed solid was washed by repeating three times an operation involving addition of 100 parts of diethyl ether, dispersion in diethyl ether using an ultrasonic washer, standing for about 15 minutes, and subsequent removal of a supernatant liquid. Subsequently, the solid was transferred to a rotary evaporator and the solvent was distilled off, so that a yellow solid was obtained. This yellow solid was dissolved in 770 parts of dichloromethane and was poured into 342 parts of a 10% aqueous potassium tris(pentafluoroethyl)trifluorophosphate solution, followed by stirring at room temperature (about 25° C.) for 2 hours. The organic layer was washed with water several times and was dried under reduced pressure, affording diphenyl-2-thioxanthonylsulfonium tris(pentafluoroethyl)trifluorophosphate in a yield of 98% and a purity of 85%. The product was identified by $^1$H-NMR, {d6-dimethyl sulfoxide, δ (ppm) 8.72 (1H, s), 8.47 (1H, d), 8.30 (1H, d), 8.13 (2H, d), 7.78-7.98 (11H, m), 7.70 (1H, t)}. The purity was determined by HPLC (the HPLC conditions were the same as those given above). Absorption caused by a P—F binding was confirmed near 840 cm$^{-1}$ by infrared spectrophotometric analysis (the KBr tablet method).

[Chem. 17]

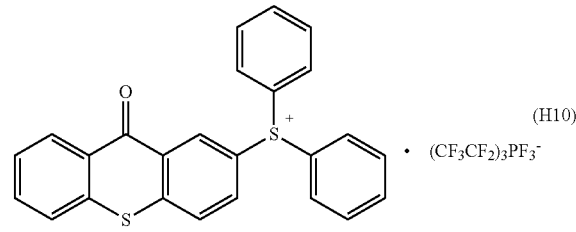

Comparative Example 2

Synthesis of 4-(phenylthio)phenyldiphenylsulfonium tris(pentafluoroethyl)trifluorophosphate (H20)

While 12.1 parts of diphenyl sulfoxide, 9.3 parts of diphenylsulfide, and 43.0 parts of methanesulfonic acid were stirred, 7.9 parts of acetic anhydride was dropped thereto, and then a reaction was performed at 40 to 50° C. for 5 hours and the reaction solution was subsequently cooled to room temperature (about 25° C.). This reaction solution was poured into 121 parts of a 20% aqueous potassium tris(pentafluoroethyl)trifluorophosphate solution and was stirred at room temperature (about 25° C.) for 1 hour, so that a slightly viscous yellow oil was precipitated. This oil was extracted with ethyl acetate and the organic layer was washed with water several times. The solvent was removed from the organic layer and toluene was added to the obtained residue to dissolve the residue. Then, hexane was added and was stirred well at 10° C. for 1 hour, followed by standing. After a lapse of 1 hour, because the solution separated into two layers, the upper layer was removed by separation. Hexane was added to the remaining lower layer and was mixed well at room temperature (about 25° C.), so that pale yellow crystals were formed. The crystals were collected by filtration and were dried under reduced pressure, affording 4-(phenylthio)phenyldiphenylsulfonium tris(pentafluoroethyl)trifluorophosphate in a yield of 60%. The product was identified by $^1$H-NMR, {(d6-dimethyl sulfoxide, δ (ppm) 7.72-7.87 (12H, m), 7.54-7.63 (5H, m), 7.42 (2H, d)}. Absorption caused by a P—F binding was confirmed near 840 cm$^{-1}$ by infrared spectrophotometric analysis (the KBr tablet method).

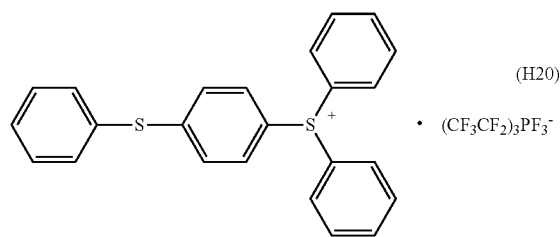

Comparative Example 3

Synthesis of diphenyl-2-thioxanthonylsulfonium hexafluoroantimonate (H30)

Diphenyl-2-thioxanthonylsulfonium hexafluoroantimonate was obtained in a yield of 97% in the same manner as in Comparative Example 1, except for changing "342 parts of a 10% aqueous potassium tris(pentafluoroethyl)trifluorophosphate solution" to "388.4 parts of 5% potassium hexafluoroantimonate." The product was identified by $^1$H-NMR, {d6-dimethyl sulfoxide, δ (ppm) 8.72 (1H, s), 8.47 (1H, d), 8.30 (1H, d), 8.13 (2H, d), 7.78-7.98 (11H, m), 7.70 (1H, t)}. Absorption caused by a Sb—F binding was confirmed near 650 cm$^{-1}$ by infrared spectrophotometric analysis (the KBr tablet method).

Comparative Example 4

Synthesis of diphenyl-2-thioxanthonylsulfonium tetrakis(pentafluorophenyl)borate (H40)

Diphenyl-2-thioxanthonylsulfonium tetrakis(pentafluorophenyl)borate was obtained in a yield of 97% in the same manner as in Comparative Example 1, except for changing "342 parts of a 10% aqueous potassium tris(pentafluoroethyl)trifluorophosphate solution" to "484.6 parts of 10% lithium tetrakis(pentafluorophenyl)borate." The product was identified by $^1$H-NMR {d6-dimethyl sulfoxide, δ (ppm) 8.72 (1H, s), 8.47 (1H, d), 8.30 (1H, d), 8.13 (2H, d), 7.78-7.98 (11H, m), 7.70 (1H, t)}. Absorption caused by a B—C binding was confirmed near 980 cm$^{-1}$ by infrared spectrophotometric analysis (the KBr tablet method).

Comparative Example 5

Synthesis of 4-(phenylthio)phenyldiphenylsulfonium tetrakis(pentafluorophenyl)borate (H50)

[4-(Phenylthio)phenyldiphenylsulfonium tetrakis(pentafluorophenyl)borate was obtained in a yield of 60% in the same manner as in Comparative Example 2, except for changing "121 parts of a 20% aqueous potassium tris(pentafluoroethyl)trifluorophosphate solution" to "342.9 parts of 10% lithium tetrakis(pentafluorophenyl)borate." The product was identified by $^1$H-NMR, {(d6-dimethyl sulfoxide, δ (ppm) 7.72-7.87 (12H, m), 7.54-7.63 (5H, m), 7.42 (2H, d)}. Absorption caused by a B—C binding was confirmed near 980 cm$^{-1}$ by infrared spectrophotometric analysis (the KBr tablet method).

Comparative Example 6

Synthesis of diphenyl-2-thioxanthonylsulfonium hexafluorophosphate (H60)

Diphenyl-2-thioxanthonylsulfonium hexafluorophosphate was obtained in a yield of 97% in the same manner as in Comparative Example 1, except for changing "342 parts of a 10% aqueous potassium tris(pentafluoroethyl)trifluorophosphate solution" to "260.1 parts of 5% potassium hexafluorophosphate." The product was identified by $^1$H-NMR {d6-dimethyl sulfoxide, δ (ppm) 8.72 (1H, s), 8.47 (1H, d), 8.30 (1H, d), 8.13 (2H, d), 7.78-7.98 (11H, m), 7.70 (1H, t)}. Absorption caused by a P—F binding was confirmed near 540 cm$^{-1}$ by infrared spectrophotometric analysis (the KBr tablet method).

Comparative Example 7

CPI-101A {a 50% propylene carbonate solution of 4-(phenylthio)phenyldiphenylsulfonium hexafluoroantimonate, produced by San-Apro, Ltd.} was used as a sulfonium salt (H70) for comparison.

Comparative Example 8

CPI-100{a 50% propylene carbonate solution of 4-(phenylthio)phenyldiphenylsulfonium hexafluorophosphonate, produced by San-Apro, Ltd.} was used as a sulfonium salt (H80) for comparison.

(Preparation and Evaluation of an Energy Ray-Curable Composition)

A sample for evaluation {the sulfonium salt obtained in Examples 1 to 12 and Comparative Examples 1 to 8} and a solvent (propylene carbonate) were mixed uniformly in the compounded amounts (part(s) by weight) given in Table 1 to prepare a sulfonium salt solution. Then, this solution and an epoxide (3,4-epoxycyclohexylmethyl-3,4-epoxycyclohexane carboxylate, produced by The Dow Chemical Co., UVR-6110) were mixed uniformly in the compounded amounts (part(s) by weight) given in Table 1 to prepare an energy ray-curable composition.

Because the sulfonium salts obtained in Examples 4, 5, and 6, and Comparative Examples 3 and 7 are hexafluoroantimonates and are lower in solubility than the tris(pentafluoroethyl)trifluorophosphates and the tetrakis(pentafluorophenyl)borates obtained in Examples 1, 2, 3, 7, 8, and 9, and Comparative Examples 1, 2, 4, and 5, the compounded amount of a solvent was set larger than the amounts of these salts. Moreover, since the sulfonium salts obtained in Examples 10, 11, and 12, and Comparative Examples 6 and 8 were hexafluorophosphates and are further lower in solubility than the hexafluoroantimonates obtained in Examples 4, 5, and 6, and Comparative Examples 3 and 7, the compounded amount of a solvent was set larger than the amounts of these salts.

TABLE 1

|  | Sulfonium salt | Solvent | Epoxide |
|---|---|---|---|
| Examples 1 to 3 | 5 | 7.5 | 100 |
| Examples 4 to 6 | 5 | 15 | 100 |
| Examples 7 to 9 | 5 | 7.5 | 100 |
| Examples 10 to 12 | 5 | 30 | 100 |
| Comparative Examples 1 and 2 | 5 | 7.5 | 100 |
| Comparative Example 3 | 5 | 15 | 100 |
| Comparative Example 7 | 5 | 15 | 100 |
| Comparative Examples 4 and 5 | 5 | 7.5 | 100 |
| Comparative Example 6 | 5 | 30 | 100 |
| Comparative Example 8 | 5 | 30 | 100 |

In each of the solvents used in Comparative Example 7 or 8, a portion of 5 parts was contained in CPI-101A or CPI-100P.

The energy ray-curable composition obtained above was applied to a polyethylene terephthalate (PET) film by using an applicator (40 μm). Using an ultraviolet irradiator, the PET film was irradiated with visible light whose wavelength was limited with a filter. Three types of filters were used. After the irradiation, a film hardness after 40 minutes, i.e., a pencil hardness (JIS K5600-5-4: 1999; corresponding International Standard ISO/DIS 15184: 1996; this document is incorporated herein by reference in its entirety) was measured, and was evaluated according to the following criteria (the thickness of the film after curing was about 40 μm). These results are shown in Tables 2 and 3. The higher the pencil hardness, the better the photocurability of the energy ray-curable composition, in other words, the better the polymerization initiating ability of the sulfonium salt to a cationically polymerizable compound (the photosensitivity of the sulfonium salt).

(Criteria)
⊚: The pencil hardness is 2H or higher.
○: The pencil hardness is H to B.
Δ: The pencil hardness is 2B to 4B.
x: The pencil hardness cannot be measured because of being liquid or having tackiness.

(Conditions of Irradiation with Visible Light)
Ultraviolet irradiator: belt conveyor type UV irradiator (manufactured by EYE GRAPHICS Co., Ltd.)
Lamp: 1.5-kW high pressure mercury lamp
Illuminance:
Condition-1a: 260 mW/cm$^2$ (measured with a 365-nm head illuminometer)
Condition-2a: 182 mW/cm$^2$ (measured with a 405-nm head illuminometer)
Condition-3a: 64 mW/cm$^2$ (measured with a 405-nm head illuminometer)
Integrated quantity of light:
Condition-1a: 150 mJ/cm$^2$ (measured with a 365-nm head illuminometer)
Condition-2a: 2300 mJ/cm$^2$ (measured with a 405-nm head illuminometer)
Condition-3a: 1940 mJ/cm$^2$ (measured with a 405-nm head illuminometer)
Condition-1b: 960 mJ/cm$^2$ (measured with a 365-nm head illuminometer)
Condition-2b: 12430 mJ/cm$^2$ (measured with a 405-nm head illuminometer)
Condition-3b: 6470 mJ/cm$^2$ (measured with a 405-nm head illuminometer)
Conditions-1b to 3b are the same as Conditions-1a to 3a except for making the irradiation time longer than Conditions-1a to 3a.

Filter:
Conditions-1a and b: 365 filter (manufactured by EYE GRAPHICS Co., Ltd., a filter capable of cutting light of 365 nm or less)
Conditions-2a and b: L-39 (manufactured by Kenko kougaku Corporation, a filter capable of cutting light of 390 nm or less)
Conditions-3a and b: L-42 (manufactured by Kenko kougaku Corporation, a filter capable of cutting light of 420 nm or less)

TABLE 2

|  |  | Cation | Anion | Photocurability | | |
|---|---|---|---|---|---|---|
|  |  |  |  | Condition-1a | Condition-2a | Condition-3a |
| Example | 1 | c1 | a1 | ⊚ | ⊚ | ⊚ |
|  | 2 | c2 | a1 | ⊚ | ⊚ | ⊚ |
|  | 3 | c3 | a1 | ⊚ | ⊚ | X |
|  | 4 | c1 | a2 | ⊚ | ⊚ | ⊚ |
|  | 5 | c2 | a2 | ⊚ | ⊚ | ⊚ |
|  | 6 | c3 | a2 | ⊚ | ⊚ | X |
|  | 7 | c1 | a3 | ⊚ | ⊚ | ⊚ |
|  | 8 | c2 | a3 | ⊚ | ⊚ | ⊚ |
|  | 9 | c3 | a3 | ⊚ | ⊚ | X |
| Comparative Example | 1 | c4 | a1 | Δ | Δ | X |
|  | 2 | c5 | a1 | X | X | X |
|  | 3 | c4 | a2 | Δ | Δ | X |
|  | 4 | c4 | a3 | Δ | Δ | X |
|  | 5 | c5 | a3 | X | X | X |
|  | 7 | c5 | a2 | X | X | X |

TABLE 3

|  |  | Cation | Anion | Photocurability | | |
|---|---|---|---|---|---|---|
|  |  |  |  | Condition-1a | Condition-2a | Condition-3a |
| Example | 10 | c1 | a4 | Δ | Δ | Δ |
|  | 11 | c2 | a4 | Δ | Δ | Δ |
|  | 12 | c3 | a4 | Δ | Δ | X |
| Comparative Example | 6 | c4 | a4 | X | X | X |
|  | 8 | c5 | a4 | X | X | X |

In Tables 2 and 3, c1 to c5 and a1 to a4 represent the following cations or anions.
c1 [4-(2-Thioxanthonylthio)phenyl]phenyl-2-thioxanthonylsulfonium
c2 Mixture of [4-(2-thioxanthonylthio)phenyl]phenyl-2-thioxanthonylsulfonium and
[4-(2-thioxanthonylthio)phenyl]diphenylsulfonium
c3 [4-(2-Thioxanthonylthio)phenyl]diphenylsulfonium
c4 Diphenyl-2-thioxanthonylsulfonium
c5 4-(Phenylthio)phenyldiphenylsulfonium
a1 Tris(pentafluoroethyl)trifluorophosphate
a2 Hexafluoroantimonate
a3 Tetrakis(pentafluorophenyl)borate
a4 Hexafluorophosphate As obvious from the results given in Tables 2 and 3, in comparison among the anions (a1 to a4), the sulfonium salts for comparison resulted in remarkably low degrees of curing of cationically polymerizable compounds with visible light of 365 nm or more, whereas the sulfonium salts of the present invention caused curing of cationically polymerizable compounds satisfactorily by the visible light.

INDUSTRIAL APPLICABILITY

The sulfonium salt of the present invention is used suitably as a photoacid generator to be used for paint, a coating agent, ink, resist (positive resist, chemically amplified resist, and negative resist), a resist film, a photosensitive material, an adhesive, a molding material, a casting material, putty, a glass fiber impregnant, a filler, a sealing material, a sealant, a material of stereolithography, and so on.

The invention claimed is:

1. A sulfonium salt represented by formula (1):

[Chem. 1]

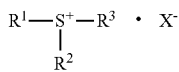

(1)

wherein $R^1$ is a group represented by formula (2); $R^2$ and $R^3$ each represent an aryl group having 6 to 30 carbon atoms, a heterocyclic hydrocarbon group having 4 to 30 carbon atoms, an alkyl group having 1 to 30 carbon atoms, an alkenyl group having 2 to 30 carbon atoms, or an alkynyl group having 2 to 30 carbon atoms, wherein some hydrogen atoms of the aryl group, the heterocyclic hydrocarbon group, the alkyl group, the alkenyl group, or the alkynyl group may be substituted with a substituent (t); S represents a sulfur atom; and $X^-$ represents a monovalent polyatomic anion:

[Chem. 2]

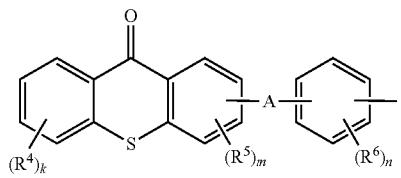

(2)

wherein $R^4$ to $R^6$ each represent an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic hydrocarbon group, an aryloxy group, an alkylsulfinyl group, an arylsulfinyl group, an alkylsulfonyl group, an arylsulfonyl group, a hydroxy (poly)alkyleneoxy group, an amino group, a cyano group, a nitro group, or a halogen atom; k, m, and n represent the number of $R^4$, the number of $R^5$, and the number of $R^6$, respectively; k is an integer of 0 to 4; m is an integer of 0 to 3; n is an integer of 0 to 4; A is a group represented by —S—, —O—, —SO—, —$SO_2$—, or —CO—; O represents an oxygen atom; and S represents a sulfur atom.

2. The sulfonium salt according to claim 1, wherein $R^2$ and $R^3$ are each an aryl group having 6 to 30 carbon atoms or a heterocyclic hydrocarbon group having 4 to 30 carbon atoms.

3. The sulfonium salt according to claim 1, wherein $R^2$ or $R^3$ is a phenyl group, A is a group represented by —S—, and k, m, and n are each 0.

4. The sulfonium salt according to claim 1, wherein $R^2$ or $R^3$ is a thioxanthonyl group, A is a group represented by —S—, and k, m, and n are each 0.

5. The sulfonium salt according to claim 1,
wherein $X^-$ is an anion represented by $MY_a^-$, $(Rf)_bPF_{6-b}^-$, $R^7_cBY_{4-c}^-$, $R^7_cGaY_{4-c}^-$, $R^8SO_3^-$, $(R^8SO_2)_3C^-$, or $(R^8SO_2)_2N^-$, wherein M represents a phosphorus atom, a boron atom, an arsenic atom, or an antimony atom; Y represents a halogen atom; Rf represents an alkyl group in which 80 mol % or more of hydrogen atoms are substituted with fluorine atoms; P represents a phosphorus atom; F represents a fluorine atom; $R^7$ represents a phenyl group in which at least one hydrogen atom is substituted with a halogen atom, a trifluoromethyl group, a nitro group, or a cyano group; B represents a boron atom; Ga represents a gallium atom; $R^8$ represents an alkyl group having 1 to 20 carbon atoms, a perfluoroalkyl group having 1 to 20 carbon atoms, or an aryl group having 6 to 20 carbon atoms; S represents a sulfur atom; O represents an oxygen atom; C represents a carbon atom; N represents a nitrogen atom; a represents an integer of 4 to 6; b represents an integer of 1 to 5; and c represents an integer of 1 to 4.

6. The sulfonium salt according to claim 1, wherein $X^-$ is an anion represented by $SbF_6^-$, $AsF_6^-$, $PF_6^-$, $BF_4^-$, $(CF_3CF_2)_3 PF_3^-$, $(C_6F_5)_4B^-$, $((CF_3)_2C_6H_3)_4B^-$, $(C_6F_5)_4Ga^-$, or $((CF_3)_2 C_6H_3)_4Ga^-$.

7. A photoacid generator comprising the sulfonium salt according to claim 1.

8. An energy ray-curable composition comprising the photoacid generator according to claim 7 and a cationically polymerizable compound.

9. A cured body obtained by curing the energy ray-curable composition according to claim 8.

* * * * *